United States Patent
Lindh et al.

(10) Patent No.: US 8,561,617 B2
(45) Date of Patent: Oct. 22, 2013

(54) IMPLANT SYSTEMS AND METHODS FOR TREATING OBSTRUCTIVE SLEEP APNEA

(75) Inventors: David C. Lindh, Flemington, NJ (US);
Robert A. Rousseau, Ottsville, PA (US);
Kevin S. Weadock, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 925 days.

(21) Appl. No.: 12/261,102

(22) Filed: Oct. 30, 2008

(65) Prior Publication Data

US 2010/0108077 A1 May 6, 2010

(51) Int. Cl.
*A61F 5/56* (2006.01)

(52) U.S. Cl.
USPC .......................... 128/848; 602/902

(58) Field of Classification Search
USPC .......... 128/848; 600/37; 623/23.72; 602/902; 433/140
See application file for complete search history.

(56) References Cited

U.S. PATENT DOCUMENTS

| | | |
|---|---|---|
| 3,123,077 A | 3/1964 | Alcamo |
| 3,378,010 A | 4/1968 | Codling et al. |
| 4,069,825 A | 1/1978 | Akiyama |
| 4,290,763 A | 9/1981 | Hurst |
| 4,557,264 A | 12/1985 | Hinsch |
| 4,839,215 A | 6/1989 | Starling et al. |
| 4,881,939 A | 11/1989 | Newman |
| 4,950,285 A | 8/1990 | Wilk |
| 5,053,047 A | 10/1991 | Yoon |
| 5,123,913 A | 6/1992 | Wilk et al. |
| 5,269,783 A | 12/1993 | Sander |
| 5,284,161 A | 2/1994 | Karell |
| 5,311,028 A | 5/1994 | Glavish |
| 5,393,984 A | 2/1995 | Glavish |
| 5,483,077 A | 1/1996 | Glavish |
| 5,484,444 A | 1/1996 | Braunschweiler et al. |
| 5,609,559 A | 3/1997 | Weitzner |

(Continued)

FOREIGN PATENT DOCUMENTS

| | | |
|---|---|---|
| CN | 2465680 | 12/2001 |
| CN | 102198010 | 9/2011 |

(Continued)

OTHER PUBLICATIONS

Shamsuzzaman, et al., "Obstructive Sleep Apnea; Implications for Cardiac and Vascular Disease", JAMA vol. 290: (14); pp. 1906-1914.

(Continued)

*Primary Examiner* — Patricia Bianco
*Assistant Examiner* — Keri J Nelson

(57) ABSTRACT

A method of treating obstructive sleep apnea includes providing an elongated element having a central buttress area and first and second arms extending from opposite ends of the central buttress area. The method includes implanting the central buttress area in a tongue so that a longitudinal axis of the central buttress area intersects an anterior-posterior axis of the tongue. The first and second arms are advanced through the tongue until the first and second arms engage inframandibular musculature. Tension is applied to the first and second arms for pulling the central buttress area toward the inframandibular musculature for moving a posterior surface of the tongue away from an opposing surface of a pharyngeal wall. The first and second arms are anchored to the inframandibular musculature for maintaining a space between the posterior surface of the tongue and the opposing surface of the pharyngeal wall.

18 Claims, 15 Drawing Sheets

(56) References Cited

U.S. PATENT DOCUMENTS

| | | |
|---|---|---|
| 5,683,417 A | 11/1997 | Cooper |
| 5,704,895 A | 1/1998 | Scott et al. |
| 5,792,067 A | 8/1998 | Karell |
| 5,843,077 A | 12/1998 | Edwards |
| 5,931,855 A | 8/1999 | Buncke |
| 6,161,541 A | 12/2000 | Woodson |
| 6,241,747 B1 | 6/2001 | Ruff |
| 6,250,307 B1 | 6/2001 | Conrad et al. |
| 6,431,174 B1 | 8/2002 | Knudson et al. |
| 6,432,437 B1 | 8/2002 | Hubbard |
| 6,457,472 B1 | 10/2002 | Schwartz et al. |
| 6,513,530 B2 | 2/2003 | Knudson et al. |
| 6,523,542 B2 | 2/2003 | Knudson et al. |
| 6,578,580 B2 | 6/2003 | Conrad et al. |
| 6,589,549 B2 | 7/2003 | Shih et al. |
| 6,599,310 B2 | 7/2003 | Leung et al. |
| 6,627,600 B2 | 9/2003 | Boutignon |
| 6,634,362 B2 | 10/2003 | Conrad et al. |
| 6,638,284 B1 | 10/2003 | Rousseau et al. |
| 6,716,251 B1 | 4/2004 | Asius et al. |
| 6,742,524 B2 | 6/2004 | Knudson et al. |
| 6,755,868 B2 | 6/2004 | Rousseau |
| 6,800,082 B2 | 10/2004 | Rousseau |
| 6,899,105 B2 | 5/2005 | Krueger et al. |
| 6,955,172 B2 | 10/2005 | Nelson et al. |
| 6,981,944 B2 | 1/2006 | Jamiolkowski et al. |
| 7,017,582 B2 | 3/2006 | Metzger et al. |
| 7,056,331 B2 | 6/2006 | Kaplan et al. |
| 7,135,189 B2 | 11/2006 | Knapp |
| 7,146,981 B2 | 12/2006 | Knudson et al. |
| 7,166,570 B2 | 1/2007 | Hunter et al. |
| 7,213,599 B2 | 5/2007 | Conrad et al. |
| 7,237,554 B2 | 7/2007 | Conrad et al. |
| 7,261,702 B1 | 8/2007 | Alexandre et al. |
| 7,288,075 B2 | 10/2007 | Parihar et al. |
| 7,297,102 B2 | 11/2007 | Smith et al. |
| 7,322,993 B2 | 1/2008 | Metzger et al. |
| 7,337,781 B2 | 3/2008 | Vassallo |
| 7,360,432 B2 | 4/2008 | Lehtonen |
| 7,360,542 B2 | 4/2008 | Nelson et al. |
| 7,367,340 B2 | 5/2008 | Nelson et al. |
| 7,401,611 B2 | 7/2008 | Conrad et al. |
| 7,442,389 B2 | 10/2008 | Quelle et al. |
| 7,601,164 B2 | 10/2009 | Wu |
| 7,669,603 B2 | 3/2010 | Knudson et al. |
| 7,806,908 B2 | 10/2010 | Ruff |
| 7,850,894 B2 | 12/2010 | Lindh, Sr. et al. |
| 7,857,829 B2 | 12/2010 | Kaplan et al. |
| 7,888,119 B2 | 2/2011 | Sugaya et al. |
| 8,142,422 B2 | 3/2012 | Makower et al. |
| 2001/0037133 A1 | 11/2001 | Knudson et al. |
| 2003/0004579 A1 | 1/2003 | Rousseau et al. |
| 2003/0149445 A1 | 8/2003 | Knudson et al. |
| 2003/0149447 A1 | 8/2003 | Morency et al. |
| 2003/0176875 A1 | 9/2003 | Anderson et al. |
| 2004/0020492 A1 | 2/2004 | Dubrul et al. |
| 2004/0020498 A1 | 2/2004 | Knudson et al. |
| 2004/0028676 A1 | 2/2004 | Klein et al. |
| 2004/0102796 A1 | 5/2004 | Hill et al. |
| 2004/0139975 A1 | 7/2004 | Nelson et al. |
| 2004/0144395 A1 | 7/2004 | Evans et al. |
| 2004/0147811 A1 | 7/2004 | Diederich et al. |
| 2004/0149290 A1 | 8/2004 | Nelson et al. |
| 2004/0153127 A1 | 8/2004 | Gordon et al. |
| 2004/0231678 A1* | 11/2004 | Fierro ............... 128/885 |
| 2005/0038472 A1 | 2/2005 | Furst |
| 2005/0082452 A1 | 4/2005 | Kirby |
| 2005/0092334 A1 | 5/2005 | Conrad et al. |
| 2005/0115572 A1 | 6/2005 | Brooks et al. |
| 2005/0121039 A1 | 6/2005 | Brooks et al. |
| 2005/0159637 A9 | 7/2005 | Nelson et al. |
| 2005/0165352 A1 | 7/2005 | Henry et al. |
| 2005/0199248 A1 | 9/2005 | Pflueger et al. |
| 2005/0203576 A1 | 9/2005 | Sulamanidze et al. |
| 2005/0251255 A1 | 11/2005 | Metzger et al. |
| 2005/0267321 A1 | 12/2005 | Shadduck |
| 2005/0267531 A1 | 12/2005 | Ruff et al. |
| 2005/0267532 A1 | 12/2005 | Wu |
| 2005/0267571 A1 | 12/2005 | Spence et al. |
| 2005/0279365 A1 | 12/2005 | Armijo et al. |
| 2006/0005843 A9 | 1/2006 | Nelson et al. |
| 2006/0079935 A1 | 4/2006 | Kolster |
| 2006/0083767 A1 | 4/2006 | Deusch et al. |
| 2006/0093644 A1 | 5/2006 | Quelle et al. |
| 2006/0150986 A1 | 7/2006 | Roue et al. |
| 2006/0185673 A1 | 8/2006 | Critzer et al. |
| 2006/0206197 A1 | 9/2006 | Morsi |
| 2006/0207608 A1 | 9/2006 | Hirotsuka et al. |
| 2006/0207612 A1* | 9/2006 | Jackson et al. ............... 128/860 |
| 2006/0228391 A1 | 10/2006 | Seyedin et al. |
| 2006/0241339 A1 | 10/2006 | Cook et al. |
| 2006/0266369 A1 | 11/2006 | Atkinson et al. |
| 2006/0289015 A1 | 12/2006 | Boucher et al. |
| 2007/0000497 A1 | 1/2007 | Boucher et al. |
| 2007/0005109 A1 | 1/2007 | Popadiuk et al. |
| 2007/0005110 A1 | 1/2007 | Collier et al. |
| 2007/0102010 A1 | 5/2007 | Lemperle et al. |
| 2007/0110788 A1 | 5/2007 | Hissong et al. |
| 2007/0119463 A1 | 5/2007 | Nelson et al. |
| 2007/0123996 A1 | 5/2007 | Sugaya et al. |
| 2007/0144531 A1 | 6/2007 | Tomas et al. |
| 2007/0144534 A1 | 6/2007 | Mery et al. |
| 2007/0144535 A1 | 6/2007 | Hegde et al. |
| 2007/0190108 A1 | 8/2007 | Datta et al. |
| 2007/0204866 A1 | 9/2007 | Conrad et al. |
| 2007/0209665 A1 | 9/2007 | Gillis et al. |
| 2007/0227545 A1 | 10/2007 | Conrad et al. |
| 2007/0233276 A1 | 10/2007 | Conrad et al. |
| 2007/0246052 A1 | 10/2007 | Hegde et al. |
| 2007/0256693 A1 | 11/2007 | Paraschac et al. |
| 2007/0257395 A1 | 11/2007 | Lindh et al. |
| 2007/0261701 A1 | 11/2007 | Sanders |
| 2007/0270631 A1 | 11/2007 | Nelson et al. |
| 2007/0272257 A1 | 11/2007 | Nelson et al. |
| 2007/0288057 A1 | 12/2007 | Kuhnel |
| 2007/0295338 A1 | 12/2007 | Loomas et al. |
| 2007/0295340 A1 | 12/2007 | Buscemi |
| 2008/0023012 A1 | 1/2008 | Dineen et al. |
| 2008/0035158 A1 | 2/2008 | Pflueger et al. |
| 2008/0035160 A1 | 2/2008 | Woodson et al. |
| 2008/0066764 A1 | 3/2008 | Paraschac et al. |
| 2008/0066765 A1 | 3/2008 | Paraschac et al. |
| 2008/0066767 A1 | 3/2008 | Paraschac et al. |
| 2008/0066769 A1 | 3/2008 | Dineen et al. |
| 2008/0078411 A1 | 4/2008 | Buscemi et al. |
| 2008/0146868 A1 | 6/2008 | Henri Robert et al. |
| 2008/0167614 A1 | 7/2008 | Tolkowsky et al. |
| 2008/0199824 A1 | 8/2008 | Hargadon |
| 2008/0208265 A1 | 8/2008 | Frazier et al. |
| 2008/0221684 A1 | 9/2008 | Nelson et al. |
| 2008/0312688 A1 | 12/2008 | Nawrocki et al. |
| 2009/0025734 A1 | 1/2009 | Doelling et al. |
| 2009/0078411 A1 | 3/2009 | Kenison et al. |
| 2009/0165803 A1 | 7/2009 | Bhat et al. |
| 2010/0023055 A1 | 1/2010 | Rousseau |
| 2010/0024830 A1 | 2/2010 | Rousseau |
| 2010/0030011 A1 | 2/2010 | Weadock |
| 2010/0037901 A1 | 2/2010 | Rousseau et al. |
| 2010/0080791 A1 | 4/2010 | Rousseau et al. |
| 2010/0106246 A1 | 4/2010 | Rousseau et al. |
| 2010/0108077 A1 | 5/2010 | Lindh et al. |
| 2010/0132719 A1 | 6/2010 | Jacobs et al. |
| 2010/0137794 A1 | 6/2010 | Knudson et al. |
| 2010/0137905 A1 | 6/2010 | Weadock et al. |
| 2010/0163056 A1 | 7/2010 | Tschopp et al. |
| 2010/0211184 A1 | 8/2010 | Rousseau et al. |
| 2010/0234794 A1 | 9/2010 | Weadock et al. |
| 2010/0234946 A1 | 9/2010 | Rousseau |
| 2010/0294284 A1 | 11/2010 | Hohenhorst et al. |
| 2010/0319710 A1 | 12/2010 | Sharkawy et al. |
| 2011/0100376 A1 | 5/2011 | Rousseau |
| 2011/0100377 A1 | 5/2011 | Weadock et al. |
| 2011/0100378 A1 | 5/2011 | Rousseau |
| 2011/0144558 A1 | 6/2011 | Rousseau |

(56) References Cited

U.S. PATENT DOCUMENTS

| | | |
|---|---|---|
| 2011/0174315 A1 | 7/2011 | Zhang et al. |
| 2011/0178439 A1 | 7/2011 | Irwin et al. |
| 2012/0245629 A1 | 9/2012 | Gross et al. |
| 2013/0074849 A1 | 3/2013 | Rousseau et al. |
| 2013/0098371 A1 | 4/2013 | Rousseau et al. |

FOREIGN PATENT DOCUMENTS

| | | |
|---|---|---|
| DE | 10245076 | 4/2004 |
| EP | 2145587 | 1/2010 |
| EP | 2517633 | 10/2012 |
| FR | 2651113 | 3/1991 |
| JP | 2003265621 | 9/2003 |
| SU | 927236 | 5/1982 |
| WO | 9900058 | 1/1999 |
| WO | 0066050 | 11/2000 |
| WO | 0121107 | 3/2001 |
| WO | 03/096928 | 11/2003 |
| WO | 2004/021869 | 3/2004 |
| WO | 2004021870 | 3/2004 |
| WO | WO 2004/020492 A1 | 3/2004 |
| WO | 2004060311 | 7/2004 |
| WO | 2004084709 | 10/2004 |
| WO | 2005046554 | 5/2005 |
| WO | 2005051292 | 6/2005 |
| WO | 2005082452 | 9/2005 |
| WO | 2007132449 | 9/2005 |
| WO | 2005122954 | 12/2005 |
| WO | 2006012188 | 2/2006 |
| WO | WO 2006/072571 A | 7/2006 |
| WO | 2006108145 | 10/2006 |
| WO | 2007056583 | 5/2007 |
| WO | 2007075394 | 7/2007 |
| WO | 2007134005 | 11/2007 |
| WO | 2007149469 | 12/2007 |
| WO | WO 2007146338 A | 12/2007 |
| WO | 2008118913 | 10/2008 |
| WO | WO 2009/023256 A | 2/2009 |
| WO | 2009036094 | 3/2009 |
| WO | WO 2010/019376 A2 | 2/2010 |
| WO | 2010/035303 | 4/2010 |
| WO | 2010065341 | 6/2010 |
| WO | 2012/041205 | 4/2012 |
| WO | 2012/064902 | 5/2012 |
| WO | WO 2012/170468 A1 | 12/2012 |

OTHER PUBLICATIONS

Schwartz, et al., "Effects of electrical stimulation to the soft palate on snoring and obstructive sleep apnea", J. Prosthetic Denistry, pp. 273-281 (1986).

Wiltfang, et al., "First results on daytime submandibular elxtrostimulation of suprahyoidal muscles to prevent night-time hypopharyngeal collapse in obstructive sleep apnea syndrome", International Journal of Oral & Maxillofacial Surgery, pp. 21-25 (1999).

Harries, et al., "The Surgical treatment of snoring", Journal of Laryngology and Otology, pp. 1105-1106 (1996).

Huang, et al., "Biomechanics of snoring", Endeavour, vol. 19 (3): pp. 96-100 (1995).

Schwab, et al., "Upper airway and soft tissue changes induced by CPAP in normal subjects", Am. J. Respit. Crit. Care Med., vol. 154, No. 4, Oct. 1996, 1106-1116.

The Advance System, Aspire Medical, Inc., www.aspiremedical.com, 3 pp. (2008).

Pang, Kenny et al., "Tongue Suspension Suture in Obstructive Sleep Apnea," Operative Techniques in Otolaryngology, vol. 17, No. 4, Dec. 2006, pp. 252-256.

Repose Genioglossus Advancement, INFLUENT Medical, www.influ.ent.com, 1 page (2008).

The Pillar Procedure, Restore Medical, Inc., www.restoremedical.com, 2 pp. (2008).

Cole et al., "Snoring: A Review and a Reassessment", Journal of Otolaryngology, pp. 303-306 (1995).

Teles et al., "Use of Palatal Lift Prosthesis on Patient Submitted to Maxillectomy: A Case Report", Applied Cancer Res. 2005, vol. 25(3), pp. 151-154.

Vicente et al., "Tongue-Base Suspension in Conjunction with Uvulopapatopharyngoplasty for Treatment of Severe Obstructive Sleep Apnea: Long-term Follow-Up Results", The Laryngoscope, vol. 115(7), pp. 1223-1227 (2006).

Wassmuth et al., "Cautery-assisted palatal stiffening operation for the treatment of obstructive sleep apnea syndrome", Otolaryngology—Head and Neck Surgery, vol. 123(1), pp. 55-60 (Jul. 2000).

Notification of Transmittal of the International Search Report and the Written Opinion of the International Search Authority or the Declaration mailed on Mar. 2, 2010; PCT/US2009/051921; International Filing Date: Jul. 28, 2009.

Notification of Transmittal of the International Search Report and the Written Opinion of the International Search Authority of the Declaration mailed on May 25, 2010; PCT/US2010/023152; International Filing Date: Feb. 2, 2010.

International Search Report dated Nov. 4, 2009 for International Patent Application No. PCT/US2009/052126.

International Search Report dated Dec. 21, 2009 for International Patent Application No. PCT/US2009/057661.

International Search Report dated Dec. 22, 2009 for International Patent Application No. PCT/US2009/061223.

International Search Report dated Apr. 29, 2010 for International Patent Application No. PCT/US2009/065293.

International Search Report dated May 25, 2010 for International Patent Application No. PCT/US2010/025778.

Schleef et al., "Cytokine Activation of Vascular Endothelium, Effects on Tissue-Type 1 Plasminogen Activator Inhibitor", The J. of Biological Chem., vol. 263, No. 12, pp. 5797-5803 (1988).

International Search Report dated Dec. 29, 2009 for International Patent Application No. PCT/US2009/061455.

International Search Report dated Jan. 21, 2010 for International Patent Application No. PCT/US2009/052110.

International Search Report dated Feb. 28, 2011 for International Patent Application No. PCT/US2010/059673.

International Search Report dated Jan. 14, 2011 for International Patent Application No. PCT/US2010/052628.

International Search Report dated Jan. 20, 2011 for International Patent Application No. PCT/US2010/052644.

International Search Report dated Jan. 24, 2011 for International Patent Application No. PCT/US2010/052649.

International Search Report dated May 25, 2010 for International patent Application No. PCT/US2010/023152.

Written Opinion dated Nov. 27, 2012 for International Patent Application No. PCT/US2012/056577.

International Search Report for International Patent Application No. PCT/US2012/061569, dated Apr. 9, 2013, 6 pp.

International Search Report for International Patent Application No. PCT/US2012/067708, dated Apr. 2, 2013, 4 pp.

Database WPI Week 198312, Thomson Scientific, Londo, GB; AN 1983-D9513K XP 002693421, -& SU 927 236 A1(Petrozazodsk Univ.), May 15, 1982 abstract (see figures 7 & 8), dated Mar. 12, 2013, 1p.

\* cited by examiner

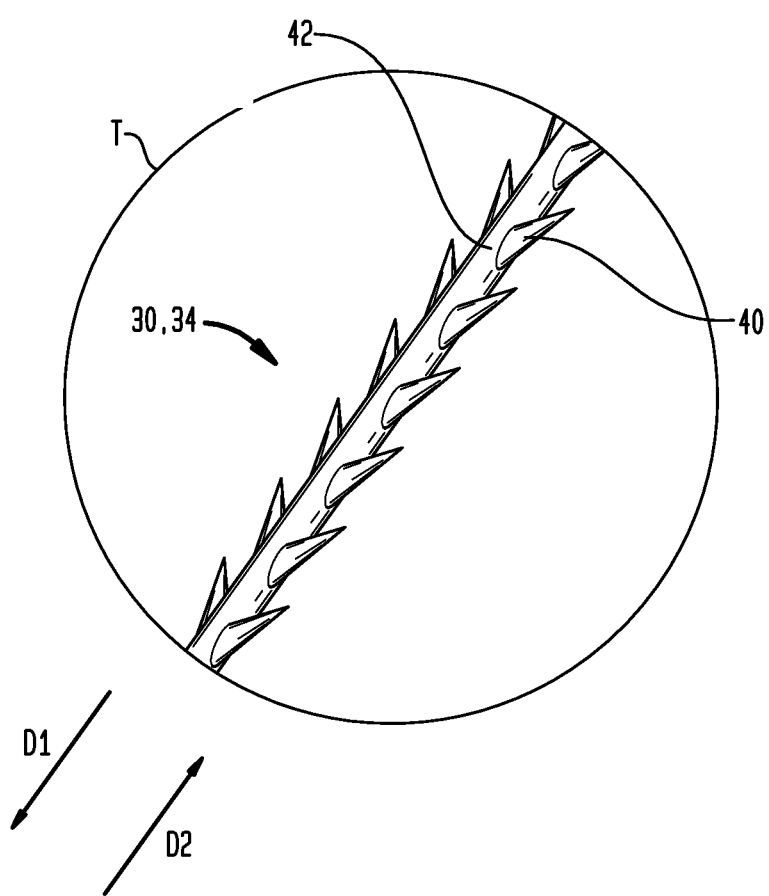

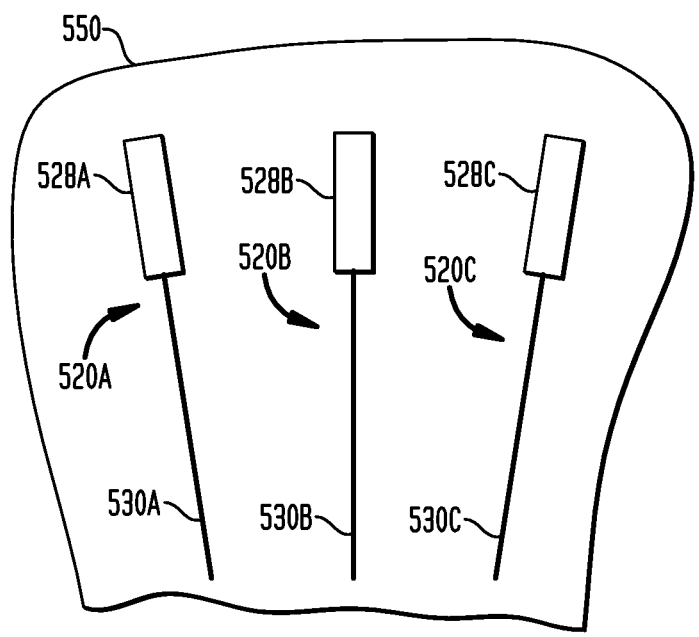
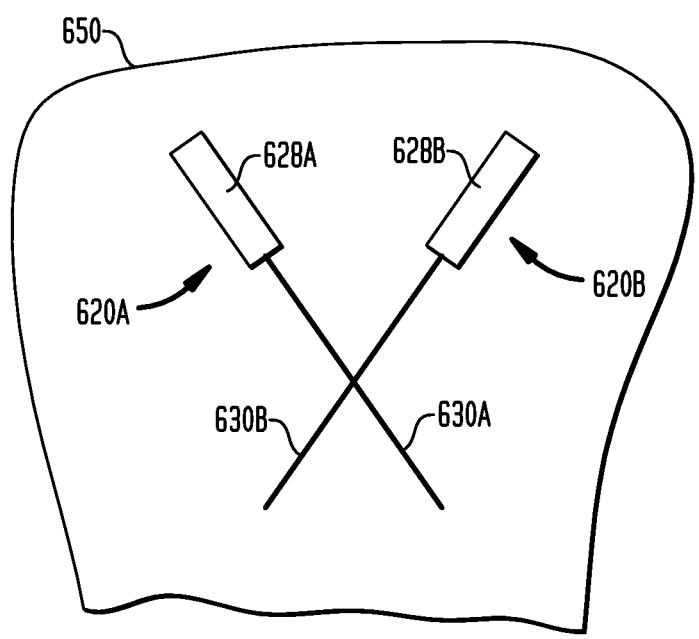

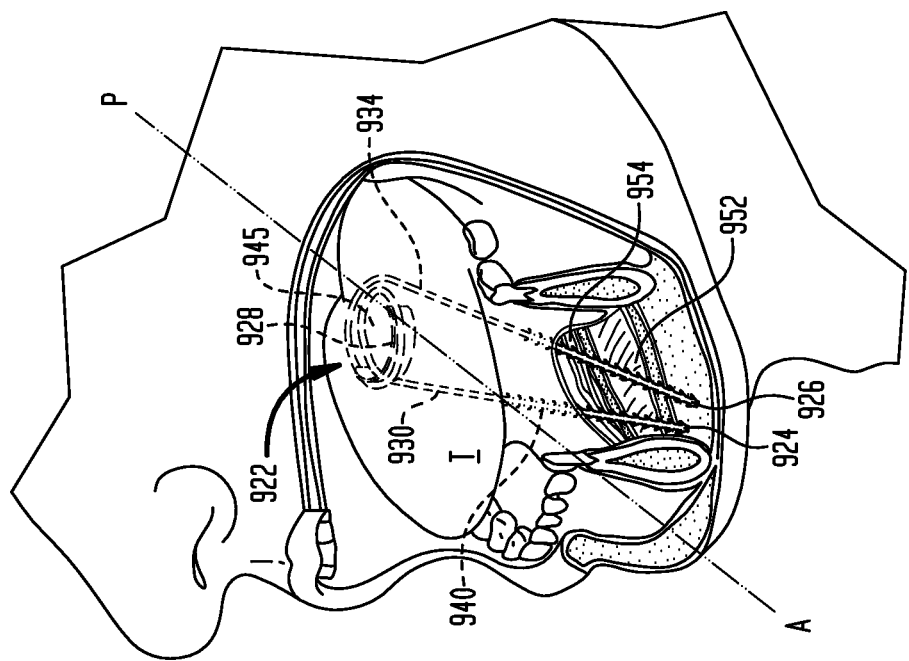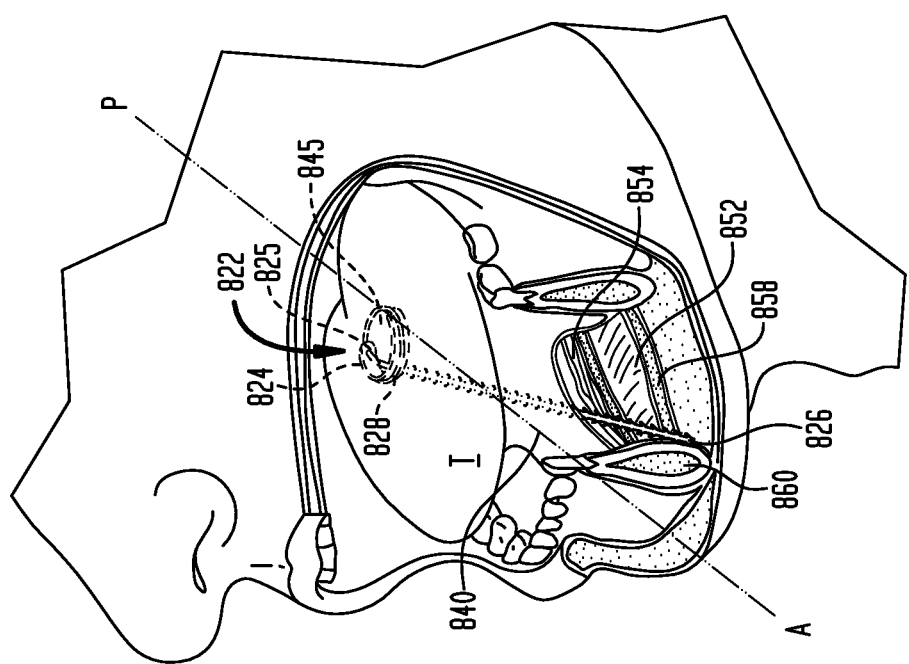

IMPLANT SYSTEMS AND METHODS FOR TREATING OBSTRUCTIVE SLEEP APNEA

BACKGROUND OF THE INVENTION

1. Field of the Invention

The present invention generally relates to treating sleep disorders, and more specifically relates to implant systems, devices and methods for treating patients suffering from obstructive sleep apnea.

2. Description of the Related Art

Obstructive sleep apnea (OSA) is caused by a blockage of the airway, which usually occurs when the soft tissue in the throat collapses and closes during sleep. According to the National Institutes of Health, OSA affects more than twelve million Americans. During each apnea event, the brain briefly arouses the sufferer in order to initiate the resumption of breathing. This type of sleep, however, is extremely fragmented and of poor quality. When left untreated, OSA may result in high blood pressure, cardiovascular disease, weight gain, impotency, headaches, memory problems, job impairment, and/or motor vehicle crashes. Despite the seriousness of OSA, a general lack of awareness among the public and healthcare professionals results in the vast majority of OSA sufferers remaining undiagnosed and untreated.

There have been a number of efforts directed to treating OSA. For example, devices for electrically stimulating the soft palate to treat snoring and obstructive sleep apnea are disclosed in U.S. Pat. Nos. 5,284,161 and 5,792,067. These devices have had mixed results because they require patient adherence to a regimen of use, subject the patient to discomfort during sleep, and result in repeated arousal of the patient.

Another treatment, commonly referred to as continuous positive airway pressure (CPAP), delivers air into a patient's airway through a specially designed nasal mask or pillow. The flow of air creates positive pressure when the patient inhales to keep the airway open. CPAP is considered by many to be an effective non-surgical treatment for the alleviation of snoring and obstructive sleep apnea, however, patients complain about discomfort caused by the mask and hoses, including bloating, nasal drying, and dry eyes. As a result, patient compliance for CPAP is only about 40%.

Surgical treatments have also been used to treat OSA. One such treatment is referred to as uvulopalatopharyngoplasty, which involves removing about 2 cm of the trailing edge of the soft palate to reduce the soft palate's ability to flutter between the tongue and the pharyngeal wall. Another procedure uses a surgical laser to create scar tissue on the surface of the soft palate, which reduces the flexibility of the soft palate for reducing snoring and/or closing of the air passage. Yet another procedure, commonly referred to as cautery-assisted palatal stiffening operation (CAPSO), is an office-based procedure performed under local anesthesia whereby a midline strip of soft palate mucosa is removed, and the wound is allowed to heal whereupon the flaccid palate is stiffened.

Surgical procedures such as those mentioned above continue to have problems. More specifically, the area of tissue that is surgically treated (i.e., removal of palatal tissue or scarring of palatal tissue) is often larger than is necessary to treat the patient's condition. In addition, the above-mentioned surgical procedures are often painful with extended, uncomfortable healing periods. For example, scar tissue on the soft palate may present a continuing irritant to the patient. Furthermore, the above procedures are not reversible in the event of adverse side effects.

Another surgical procedure for treating OSA uses several braided PET cylinders that are implanted in tissue to make the tissues of the tongue or uvula more rigid and less prone to deflection. The Pillar™ Palatal Implant System sold by Restore Medical of St. Paul, Minn. consists of cylindrical-shaped elements of braided polyester filaments that are implanted in the soft palate for reducing the incidence of airway obstructions in patients suffering from mild to moderate OSA. The Pillar device has been associated with a number of adverse side effects, including extrusion of the cylindrical-shaped elements, infection, and patient discomfort.

Another implant system, sold under the trademark REPOSE™ by InfluENT of Concord, N.H., uses a titanium bone screw that is inserted into the posterior aspect of the mandible at the floor of the mouth. A loop of suture is passed through the tongue base and attached to the mandibular bone screw. The Repose™ procedure achieves a suspension or hammock of the tongue base making it less likely for the base of the tongue to prolapse during sleep. Due to the high activity of the tongue during wakefulness, however, the suture component of this device may act as a "cheese cutter" to the tongue, causing device failure and requiring subsequent removal.

Another effort for treating OSA involves creating an auxiliary airway for bypassing the clogged portion of the main airway. In one embodiment of commonly assigned U.S. patent application Ser. No. 12/182,402, filed Jul. 30, 2008, the disclosure of which is hereby incorporated by reference herein, an auxiliary airway is formed by implanting an elongated conduit beneath a pharyngeal wall of the pharynx. The elongated conduit has a proximal end in communication with a first region of the pharynx, a distal end in communication with a second region of the pharynx, and an intermediate section extending beneath the pharyngeal wall for bypassing an oropharynx region of the pharynx.

Magnets have also been used for treating OSA. For example, in one embodiment of commonly assigned U.S. patent application Ser. No. 12/183,955, filed Jul. 31, 2008, the disclosure of which is hereby incorporated by reference herein, a magnetic implant includes a bone anchor, a first magnet coupled to the bone anchor, a tongue anchor, a second magnet coupled to the tongue anchor, and a support for aligning the first and second magnets so that a repelling force is generated between the magnets for urging the second magnet away from the first magnet and toward the bone anchor. The support maintains the first magnet at a fixed distance from the bone anchor, aligns the first magnet with the second magnet, and guides movement of the first and second magnets. The magnetic implant disclosed in one or more embodiments of the '955 application does not have a hard stop so as to avoid the "cheese-cutter" effect observed when using implants having a hard stop.

In spite of the above advances, there remains a need for additional systems, devices and methods for treating OSA through minimally invasive approaches that provide long term results, that encourage patient compliance, and that minimize patient discomfort.

SUMMARY OF THE INVENTION

In one embodiment, a method of treating obstructive sleep apnea includes providing an elongated element having a central area, a first arm extending from a first end of the central area, and a second arm extending from a second end of the central area, and implanting the central area of the elongated element in a tongue. After implanting the central area of the elongated element in the tongue, the first and second arms are preferably advanced through the tongue until the first and second arms engage inframandibular musculature. As used herein, the term "inframandibular musculature" generally refers to the geniohyoid, mylohyoid, digastric and pterygoid muscles. Tension is preferably applied to the first and second arms for pulling the center area of the elongated element toward the inframandibular musculature, which, in turn, moves a posterior surface of the tongue away from an opposing surface of a pharyngeal wall. In one embodiment, after the tension is applied, the first and second arms are desirably anchored to the inframandibular musculature for maintaining a space between the posterior surface of the tongue and the opposing surface of the pharyngeal wall.

In one embodiment, the central area of the elongated element preferably includes a buttress defining a larger width region of the elongated element. The width of the central, buttress area is preferably greater than the diameter of the first and second arms. In one embodiment, after the implanting step, the buttress desirably extends along an axis that traverses an anterior-posterior axis of the tongue. In one embodiment, the buttress area extends laterally in an oral cavity and substantially perpendicular to the anterior-posterior axis of the tongue.

In one embodiment, the method desirably includes implanting a second buttress in the inframandibular musculature and coupling the first and second arms with the second buttress. The first and second buttresses may be secured to each other. In one embodiment, the second buttress is implanted in the inframandibular musculature. The base may include a tensioning element coupled with the first and second arms for applying tension to the first and second arms. The tensioning element may be rotatable using a tool such as a screw driver or an L-shaped wrench.

In one embodiment, the elongated element includes a first set of barbs projecting from the first arm and a second set of barbs projecting from the second arm. The first and second set of barbs may project away from one another in opposite directions. The elongated element may include a braided cylinder or sleeve and the first and second barbs may extend through interstices of the braided sleeve.

In one embodiment, at least one of the first and second arms may be anchored to thyroid cartilage. In one embodiment, at least one of the first and second arms may be looped around a hyoid bone or be disposed adjacent to or in contact with the hyoid bone. In one embodiment, a first region of an elongated element may have one or more sets of barbs and another region of the elongated element may have one or more loops. The barbed first region may be passed through the loops in the second region.

In one embodiment, a method of treating obstructive sleep apnea includes providing an elongated element having a central buttress area, a first arm extending from a first end of the central buttress area, and a second arm extending from a second end of the central buttress area. The central buttress area preferably has a larger cross-sectional width than the first and second arms for improving anchoring of the central buttress area in tissue (e.g. tongue tissue) and to provide an increased load bearing area. The method desirably includes implanting the central buttress area of the elongated element in a tongue so that a longitudinal axis of the central buttress area intersects an anterior-posterior axis of the tongue. After the central buttress area is implanted, the first and second arms are preferably advanced through the tissue of the tongue until the first and second arms engage inframandibular musculature. The method may include applying tension to the first and second arms for pulling the previously implanted central buttress area toward the inframandibular musculature so as to move a posterior surface of the tongue away from an opposing surface of a pharyngeal wall. The first and second arms may be anchored or secured to the inframandibular musculature for maintaining a space between the posterior surface of the tongue and the opposing surface of the pharyngeal wall so as to avoid OSA episodes. In one embodiment, the method may include looping at least one of the first and second arms around a hyoid bone. In one embodiment, at least one of the first and second arms may also be passed through the thyroid cartilage.

In one embodiment, the first arm preferably has a first set of barbs projecting therefrom and the second arm preferably has a second set of barbs projecting therefrom. The first and second sets of barbs preferably project away from one another. In one embodiment, the elongated element may include a braided element with a first set of barbs projecting from the first arm and through the braided element, and a second set of barbs projecting from the second arm and through the braided element.

In one embodiment, a method of treating obstructive sleep apnea may include implanting a second buttress in or near the inframandibular musculature and coupling the first and second arms with the second buttress. In one embodiment, the second buttress preferably extends along an axis that intersects the anterior-posterior axis of the tongue. The first and second buttresses may extend along axes that are parallel with one another and that are substantially perpendicular with the anterior-posterior axis of the tongue.

In one embodiment, a method of treating obstructive sleep apnea includes providing an elongated element having a buttress, a first arm extending from a first end of the buttress, and a second arm extending from a second end of the buttress, whereby the buttress has a cross-sectional width that is larger than respective cross-sectional diameters of the first and second arms. The method desirably includes implanting the buttress in a tongue, and after implanting the buttress, advancing the first and second arms through the tongue until the first and second arms engage inframandibular musculature. Tension may be applied to the first and second arms for pulling the buttress toward the inframandibular musculature so as to move a posterior surface of the tongue away from an opposing surface of a pharyngeal wall. The first and second arms may be anchored to the inframandibular musculature for maintaining a space between the posterior surface of the tongue and the opposing surface of the pharyngeal wall. In one embodiment, one or more buttresses may be implanted in the inframandibular musculature and the free ends of the first and second arms may be coupled with the one or more buttresses.

In one embodiment, an implant device may include a braided, barbed suture or an expanded porous cylinder, barbed suture having a buttress component that is implanted in the tongue. The implant preferably includes two arms that extend from the buttress component. In one embodiment, the two arms may be barbed. In one embodiment, the two arms may not have barbs. In one embodiment, the two arms are preferably adapted for extending to inframandibular musculature, a hyoid bone or thyroid cartilage. The center of the buttress is desirably adapted for implantation into the posterior region of the tongue base, and the free ends of each of the arms may be connected to respective tissue penetrating elements such as needles that facilitate placement and securement of the implant device. The center of the buttress is preferably expanded at the point that is implanted in the tongue. In one embodiment, the expansion results from placing a biocompatible element within the core of the elongated element, such as within the core of a braided elongated element. The biocompatible element may have an elliptical shape, may be placed within a previously braided suture, or may be inserted during a braiding process used to form the implant device.

In one embodiment, the proximal and distal ends of the braided arms may be modified to include barbed elements projecting therefrom so as to enhance anchoring of the arms in tissue upon implantation. In one embodiment, needles may be secured to the distal ends of the arms. A barbed element may be placed in the core of the braid or the braid may be formed around the barbed element. In one embodiment, the barbs preferably exit through the interstices of the braid so as to provide for enhanced tissue fixation to the hyoid bone, thyroid cartilage, and/or other tissues such as muscles or fascia in the inframandibular region. In one embodiment, the barbs may serve as a means for attaching the implant device to additional buttress components implanted in inframandibular musculature and/or soft tissue or cartilage located near the inframandibular musculature. In one embodiment, the barbs preferably serve as a "soft anchor" for an intra-tongue implant, whereby the support arms may be adjusted to prevent the tongue from sealing against the posterior wall of the pharynx for treating obstructive sleep apnea.

In one embodiment, a barbed device with a buttress in the center is implanted within a patient's mouth. The procedure may be performed on an outpatient basis or require a one night hospital stay. The tension on the arms coupled with the center buttress may be adjusted by a surgeon at the time of implantation and will serve to prevent the tongue from sealing against the posterior wall of the pharynx. In one embodiment, by securing the arms to soft tissue such as the inframandibular muscles, the "cheese cutter" effect that occurs when anchoring to a hard stop is avoided. Avoiding the "chess cutter" effect may also be achieved by securing the support arms to the floating hyoid bone.

In one embodiment, one or more additional buttresses are placed in the inframandibular musculature such as the geniohyoid and/or mylohyoid muscles and the arms extending from the center of the implant are coupled with the one or more additional buttresses. Additional buttresses may be placed at various tissue sites either before or after the central buttress within the tongue has been deployed. A surgeon may place small incisions within creases of skin and place the other buttress components at desired locations in a minimally invasive manner. The entire system may be locked in place by using self-locking devices or a tensioning mechanism that allows the surgeon to adjust each buttress independently, or by using self-locking nuts. In one embodiment, a three-buttress concept may be used independently with no center attachment device. In one embodiment, the buttresses may be coupled together.

In one embodiment, the materials used for forming the buttresses may include biocompatible materials such as non-resorbable and resorbable polymers. Suitable non-resorbable polymers may include silicone, polyethylene terephalate, polytetrafluoroethylene, polyurethane and polypropylene. Suitable resorbable polymers may include polylactide, polyglycolide copolymers, polycaprolactone, and collagen. In addition, materials such as nitinol, stainless steel, or resorbable alloys such as magnesium or iron alloys may be used to form the buttresses. In one embodiment, bladders of electrorheologic or magnetorheologic materials may also be placed within the center of the braid. The stiffness of these materials may be altered by placing a magnet or electric field at a desired location such as in the soft palate or the posterior pharyngeal wall. The necessary magnetic or electric field may be applied by an external source and may be transmitted percutaneously to the materials by inductive coupling.

In one embodiment, buttressed implants may be placed at various angles within the tongue to provide an optimal effect for opening an airway. In one embodiment, an implant may be placed parallel to the midline of the tongue.

In one embodiment, a method of treating obstructive sleep apnea includes wrapping an elongated element around a bundle of fibers extending through a tongue so as to form at least one loop around the bundle of fibers, compressing the bundle of fibers using the at least one loop, and coupling a tether with the elongated element. The method desirably includes advancing a free end of the tether toward inframandibular musculature, applying tension to the tether for pulling the looped elongated element toward the inframandibular musculature so as to move a posterior surface of the tongue away from an opposing surface of a pharyngeal wall, and anchoring the tether to the inframandibular musculature. In one embodiment, the tether is integrally formed with the elongated element.

These and other preferred embodiments of the present invention will be described in more detail below.

BRIEF DESCRIPTION OF THE DRAWING

FIGS. 5A-5B show the implant of the FIGS. 4A-4C after implantation in a patient, in accordance with one embodiment of the present invention.

FIG. 13 shows a system for treating obstructive sleep apnea, in accordance with one embodiment of the present invention.

FIG. 14 shows a system for treating obstructive sleep apnea, in accordance with one embodiment of the present invention.

FIG. 16 shows an implant for treating obstructive sleep apnea, in accordance with one embodiment of the present invention.

FIG. 17 shows an implant for treating obstructive sleep apnea, in accordance with one embodiment of the present invention.

DETAILED DESCRIPTION

Figure 1:
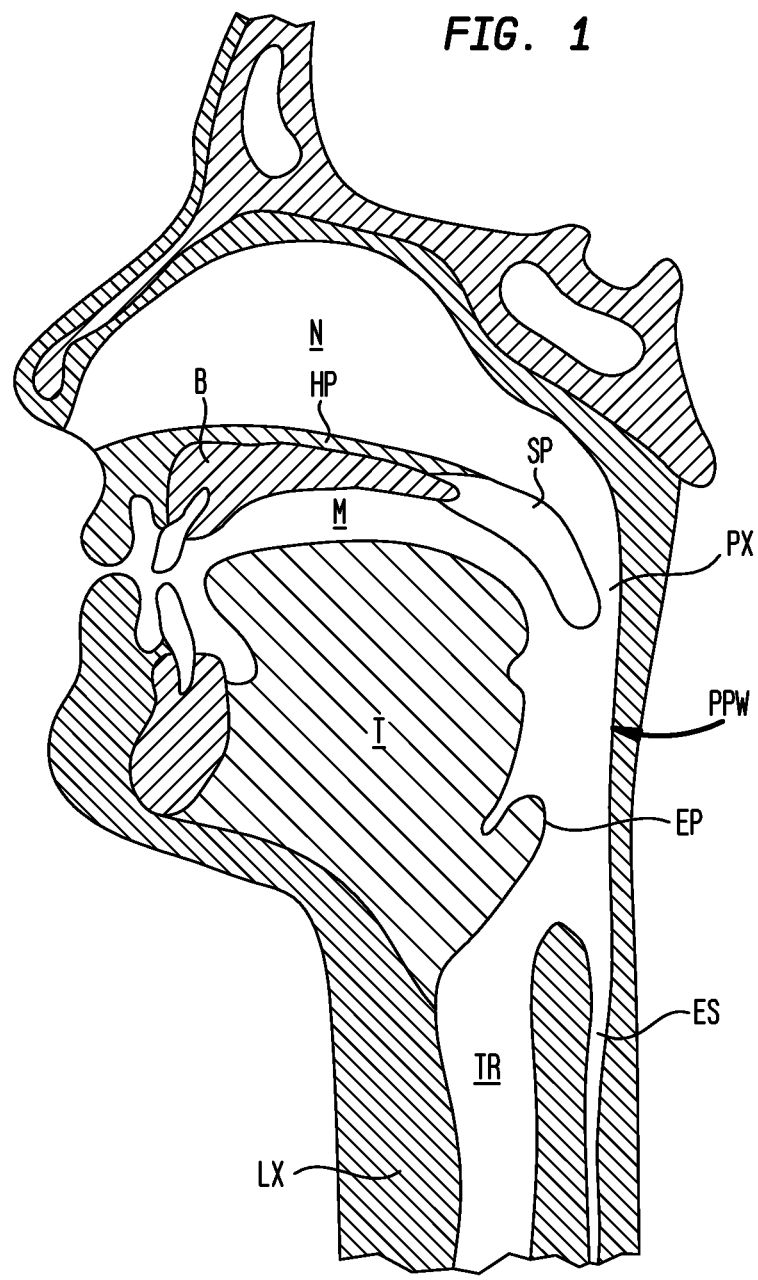
FIG. 1 shows a cross-sectional view of a human head including a nasal cavity and a pharynx.

FIG. 1 shows a cross-section of a human head with anatomical structures including the nasal cavity N, bone B of the hard palate HP, the soft palate SP, the mouth M, the tongue T, the trachea TR, the epiglottis EP, the esophagus ES, and the posterior pharyngeal wall PPW.

Figure 2:
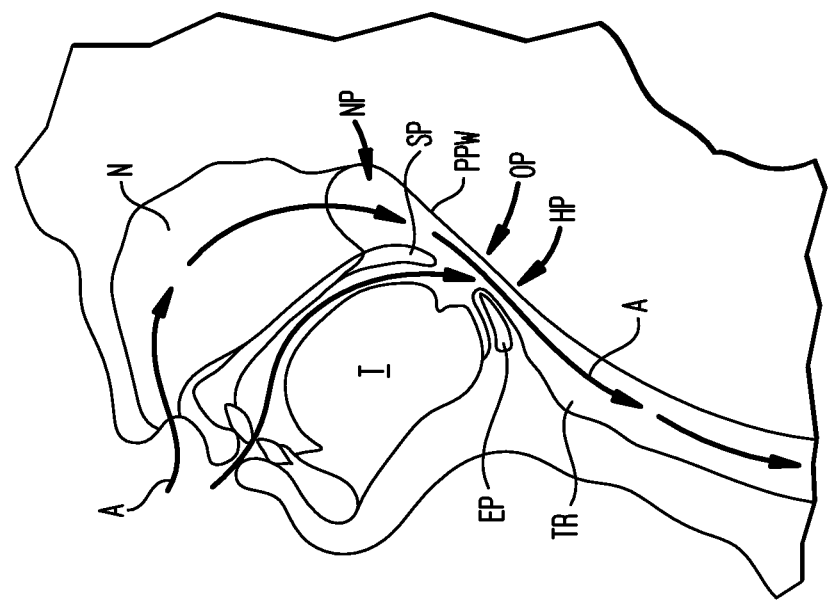
FIG. 2 shows a cross-sectional view of the nasal cavity and the pharynx of a human during normal breathing.

In a human body, an air filled space between the nasal cavity N and the larynx LX is referred to as the upper airway. The most critical part of the upper airway associated with sleep disorders is the pharynx PX. Referring to FIG. 2, the pharynx has three different anatomical levels. The nasopharynx NP is the upper portion of the pharynx located in the back of the nasal cavity N. The oropharynx OP is the intermediate portion of the pharynx containing the soft palate SP, the epiglottis EP, and the curve at the back of the tongue T. The hypopharynx HP is the lower portion of the pharynx located below the soft tissue of the oropharynx OP. The oropharynx OP is the section of the pharynx that is most likely to collapse due to the high prevalence of soft tissue structure, which leaves less space for airflow. The hypopharynx HP lies below the aperture of the larynx and behind the larynx, and extends to the esophagus.

As is well known to those skilled in the art, the soft palate and the tongue are both flexible structures. The soft palate SP provides a barrier between the nasal cavity N and the mouth M. In many instances, the soft palate SP is longer than necessary and extends a significant distance between the back of the tongue T and the posterior pharyngeal wall PPW.

Although the muscles relax throughout the body during sleep, most of the muscles of the respiratory system remain active. During inhalation, the diaphragm contracts and causes negative pressure to draw air A into the nasal cavity N and the mouth M. The air then flows past the pharynx PX, through the trachea TR and into the lungs. The negative pressure causes the tissue of the upper airway to deform slightly, which narrows the airway passage. In apneic patients, the soft palate SP, the tongue T, and/or the epiglottis EP collapse against the posterior pharyngeal wall PPW to block airflow into the trachea. As the airway narrows, airflow through the pharynx becomes turbulent which causes the soft palate SP to vibrate, generating a sound commonly known as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep.

If apnea or hypopnea occurs more than five times per hour, most medical personnel diagnose the individual as having an upper airway resistance problem. Many of these patients often exhibit symptoms related to sleep disorders including sleepiness during the day, depression, and difficulty concentrating.

Individuals having ten or more episodes of apnea or hypopnea during every hour of sleep are officially classified as having obstructive sleep apnea syndrome. As the airway is obstructed, the individual makes repeated attempts to force inhalation. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or awakening with a choking feeling.

Figure 3:
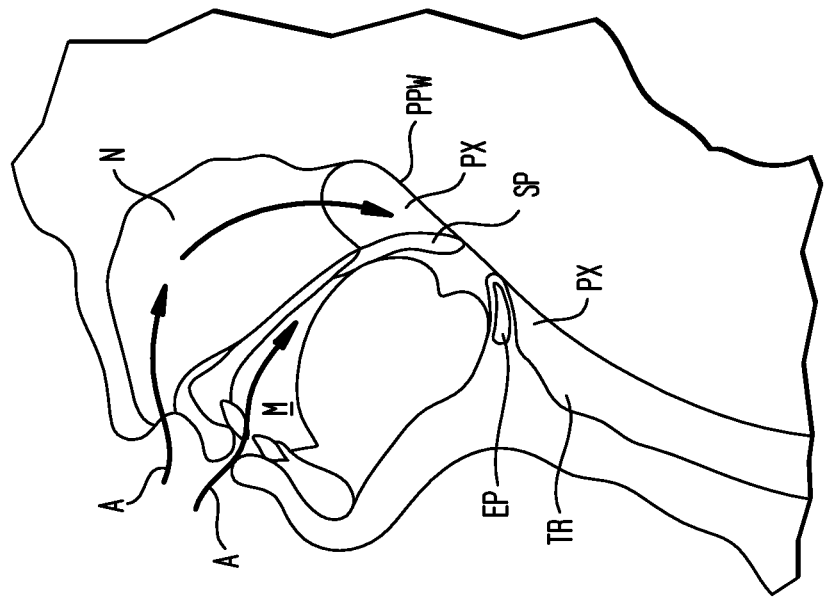
FIG. 3 shows a cross-sectional view of the nasal cavity and the pharynx of a human during an obstructive sleep apnea episode.

Referring to FIG. 2, when an individual is awake, the back of the tongue T and the soft palate SP maintain their shape and tone due to their respective internal muscles. As a result, the airway A through the pharynx remains open and unobstructed. During sleep, however, the muscle tone decreases and the posterior surface of the tongue and the soft palate become more flexible and distensible. Referring to FIG. 3, without normal muscle tone to keep their shape and to keep them in place either alone or as a group, the posterior surface of the tongue T, the epiglottis EP, and the soft palate SP tend to easily collapse to block the airway A.

Figure 4A:
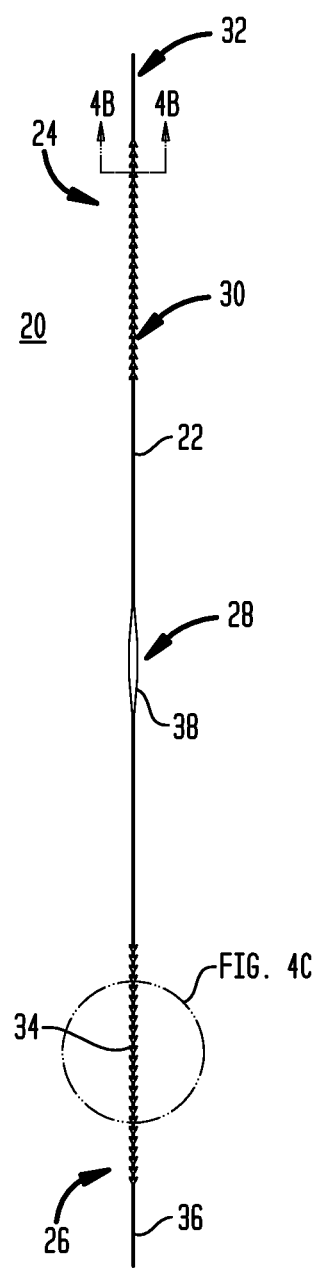
FIGS. 4A-4C show an implant for treating obstructive sleep apnea, in accordance with one embodiment of the present invention.

Referring to FIG. 4A, in one embodiment, an implant 20 used for treating obstructive sleep apnea includes an elongated element 22 such as a barbed suture having a first end 24 and a second end 26. The elongated element 22 preferably includes a buttress 28 at a center portion thereof, a first arm 30 located between the buttress 28 and the first end 24, and a first needle 32 secured to the free end of the first arm 30. The elongated element 22 also preferably includes a second arm 34 extending between the buttress 28 and the second end 26 thereof, and a second needle 36 secured to the free end of the second arm 34. In one embodiment, the buttress 28 desirably forms the widest portion of the implant.

Figure 4B:
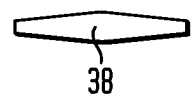

Referring to FIGS. 4A and 4B, in one embodiment, the center of the buttress area 28 desirably includes a biocompatible element 38 disposed therein. In one embodiment, the biocompatible element 38 has an elliptical shape and may be placed within a previously implanted elongated element or may be inserted into the center of the elongated element before implanting the elongated element in tissue. The elongated element may be formed from only non-absorbable materials or may include absorbable materials. The non-absorbable materials may include polymeric materials such as non-resorbable polymers, silicone, polyethylene terephalate, polytetrafluoroethylene, polyurethane and polypropylene, nitninol, stainless steel, and/or composite materials. Suitable resorbable polymers may include polylactide, polyglycolide copolymers, polycaprolactone, and/or collagen. The biocompatible element 38 may also comprise a biocompatible metal or alloy.

Figure 4C:
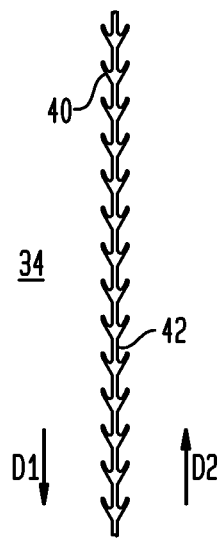

FIG. 4C shows the second arm 34 of the elongated element 22. In one embodiment, each of the first and second arms 24, 34 preferably include a plurality of barbs 40 that project from a flexible core 42. The plurality of barbs 40 are desirably spaced from one another along the length of the flexible core 42. In one embodiment, the tips of the sequentially positioned barbs 40 are about 0.060 inches from one another. In one embodiment, the barbs 40 are adapted to collapse inwardly when pulled through tissue in a first direction $D_1$, and to engage the tissue for holding the second arm 34 in place when pulled in a second direction $D_2$. In one embodiment, the barb base portions may be staggered along the axis of the arm elements to either partially oppose each other or to prevent direct opposition of any two barbs through the axis of the arm element.

The particular embodiment shown in FIGS. 4A-4C is a monofilament having the barbs cut therefrom. In other embodiments, however, the elongated element may include a braided element without barbs, a braided element with barbs, a woven structure with or without barbs, and/or a circular knit structure with or without barbs. In certain preferred embodiments, the elongated element may incorporate one or more of the features disclosed in commonly assigned U.S. Patent Application Publication Nos. 20070005109 and 20070005110, the disclosures of which are hereby incorporated by reference herein.

Figure 5A:
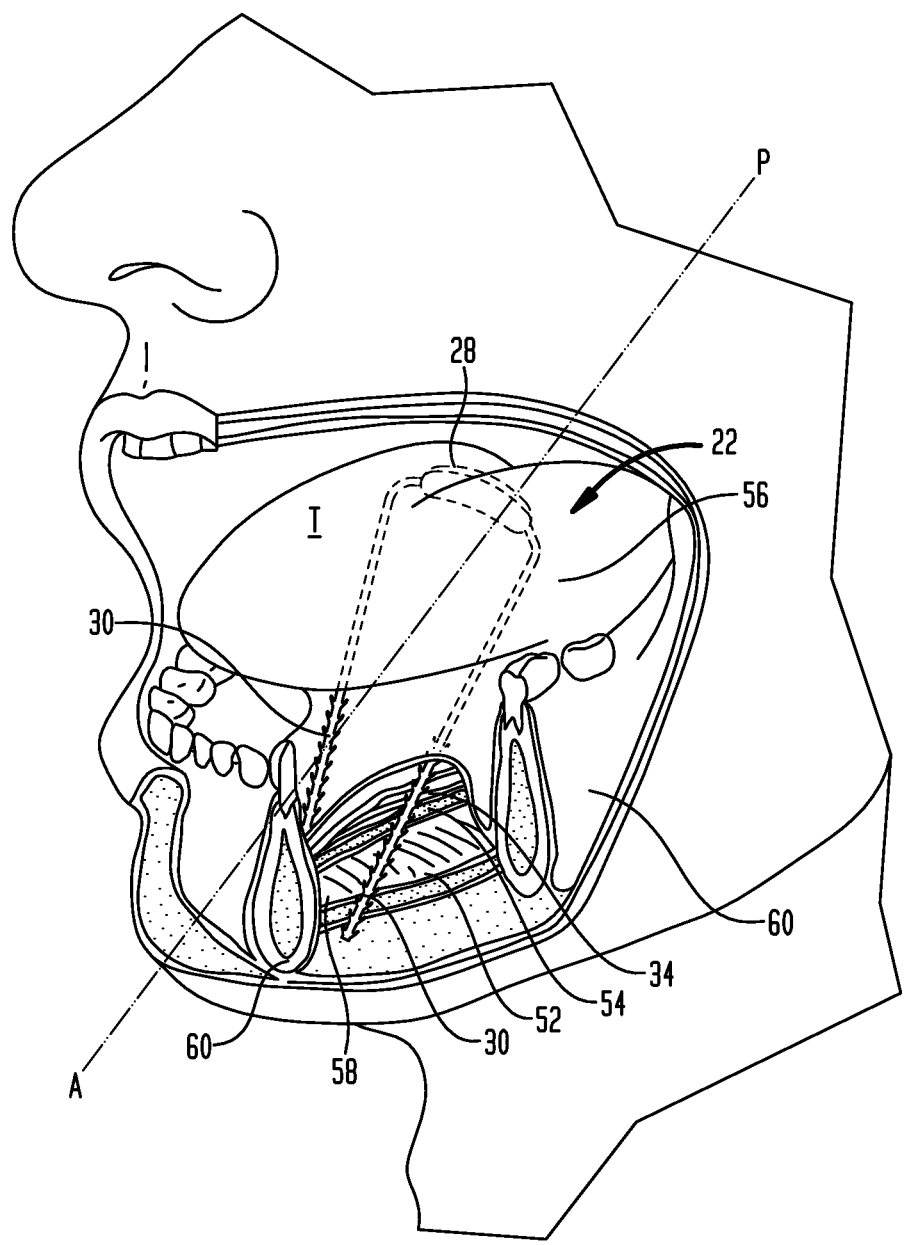

Referring to FIG. 5A, in one embodiment, the elongated element 22 shown in FIGS. 4A-4C is implanted within the oral cavity of a patient. As shown in FIG. 5A, an oral cavity typically includes a body of a tongue T, a mylohyoid muscle 52, a geniohyoid muscle 54, and a genioglossus muscle 56. The mylohyoid muscle 52 has an anterior end 58 anchored to a mandible 60 and a posterior end anchored to a hyoid bone (not shown). Referring to FIG. 5A, in one embodiment, the implant is preferably positioned within the tongue T so that the buttressed section 28 is located in the center of the tongue body and extends laterally toward the sides of the oral cavity. In one embodiment, the buttress area 28 extends along an axis that traverses or is substantially perpendicular with an anterior-posterior axis (designated A-P) of the tongue T. The center buttressed section 28 preferably has a large surface area for holding the implant in place so as to avoid the "cheese cutter" effect present when using implants with immovable anchor positions. The first arm 30 of the implant desirably extends from the buttressed section 28 toward the anterior end 58 of the mylohyoid muscle 52. The second arm 34 also desirably extends from the buttressed section 28 toward the anterior end 58 of the mylohyoid muscle 52.

Referring to FIG. 5B, in one embodiment, one or more of the arms 30, 34 extending through the tissue of the tongue T preferably includes a flexible core 42 and a plurality of barbs 40 projecting outwardly from the flexible core 42. The barbs 40 preferably collapse inwardly toward the core 42 as the arm is pulled in the direction designated $D_1$. The barbs 40 project outwardly when the arm is pulled in the direction designated $D_2$ for holding the arm 30 in place in the tongue tissue. Although the present invention is not limited by any particular theory of operation, it is believed that the barbs enhance anchoring of the implant in tissue.

Figure 6:
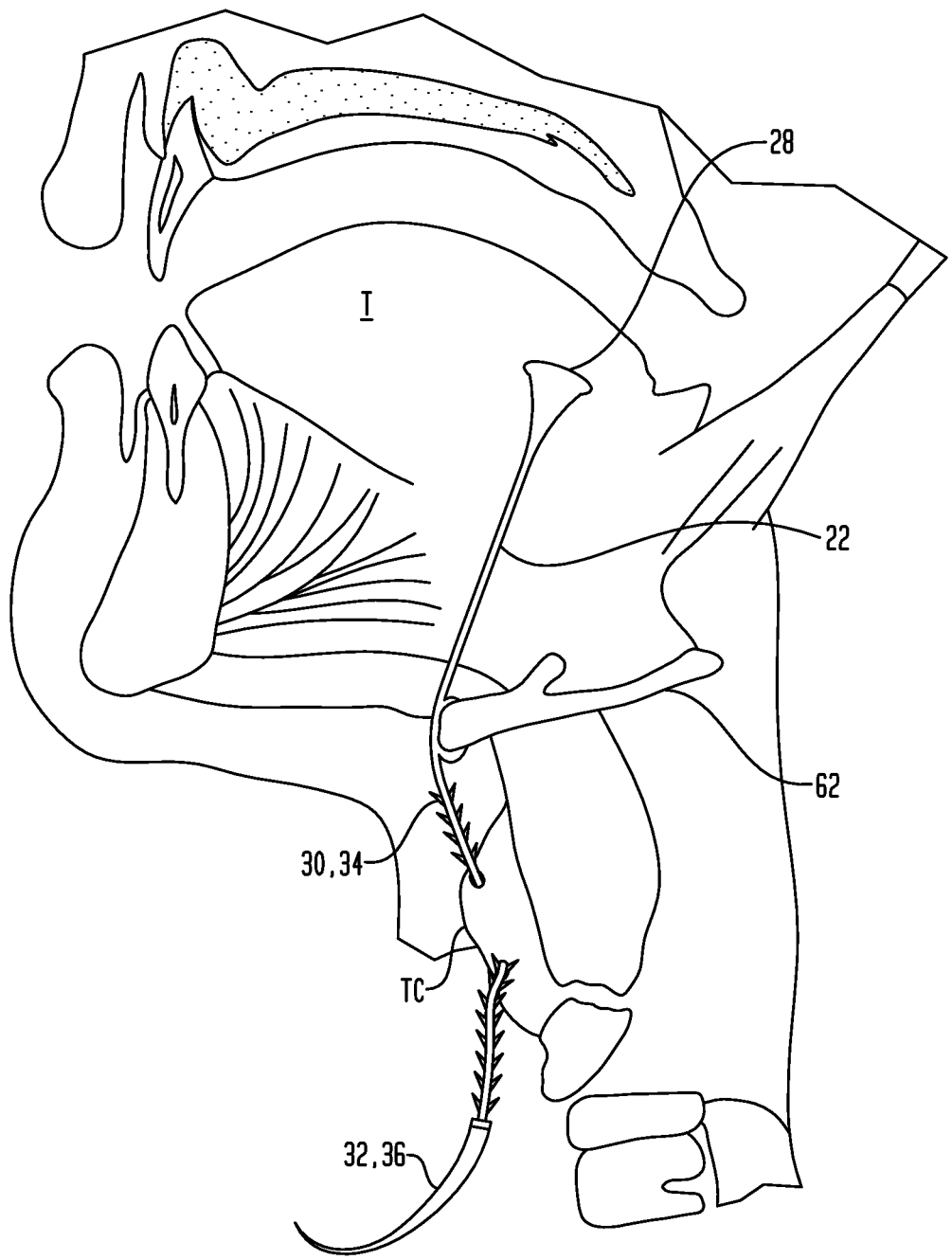
FIG. 6 shows a cross-sectional side view of a human head including a nasal cavity after implantation of the implant of FIGS. 4A-4C, in accordance with one embodiment of the present invention.

FIG. 6 shows a sagital cross-section of a patient's head after the elongated element of FIGS. 4A-4C has been implanted therein. The elongated element 22 includes the center buttressed section 28, wider than the first and second arms 30, 34 of the device, implanted in the patient's tongue T. The first and second barbed arms 30, 34 extend through the tissue of the oral cavity toward the lower end of the oral cavity. In FIG. 6, only one of the arms 30, 34 is visible due to the sagital view. The needles 32, 36 are used for advancing the barbed first and second arms 30, 34 through the tissue. In one embodiment, the first and second barbed arms 30, 34 may be looped around the hyoid bone 65 and the needles 32, 36 needles may be passed through the thyroid cartilage TC of the patient. In one embodiment, the two barbed arms 30, 34 are preferably adapted for extending to the hyoid bone or the thyroid cartilage. The center of the buttress 28 is preferably adapted to be implanted in the posterior region of the tongue T, and the distal ends of each of the barbed arms 30, 34 may be connected to a needle that facilitates placement and securement of the implant device. The center of the buttressed section 28 is preferably expanded at the point that it is implanted in the tongue. The expansion may result from placing a biocompatible element within the core of the barbed element, such as an elliptical shaped biocompatible element. The biocompatible element may be placed within a previously implanted braided suture or may be inserted during the braiding process to form the device.

Figure 7:
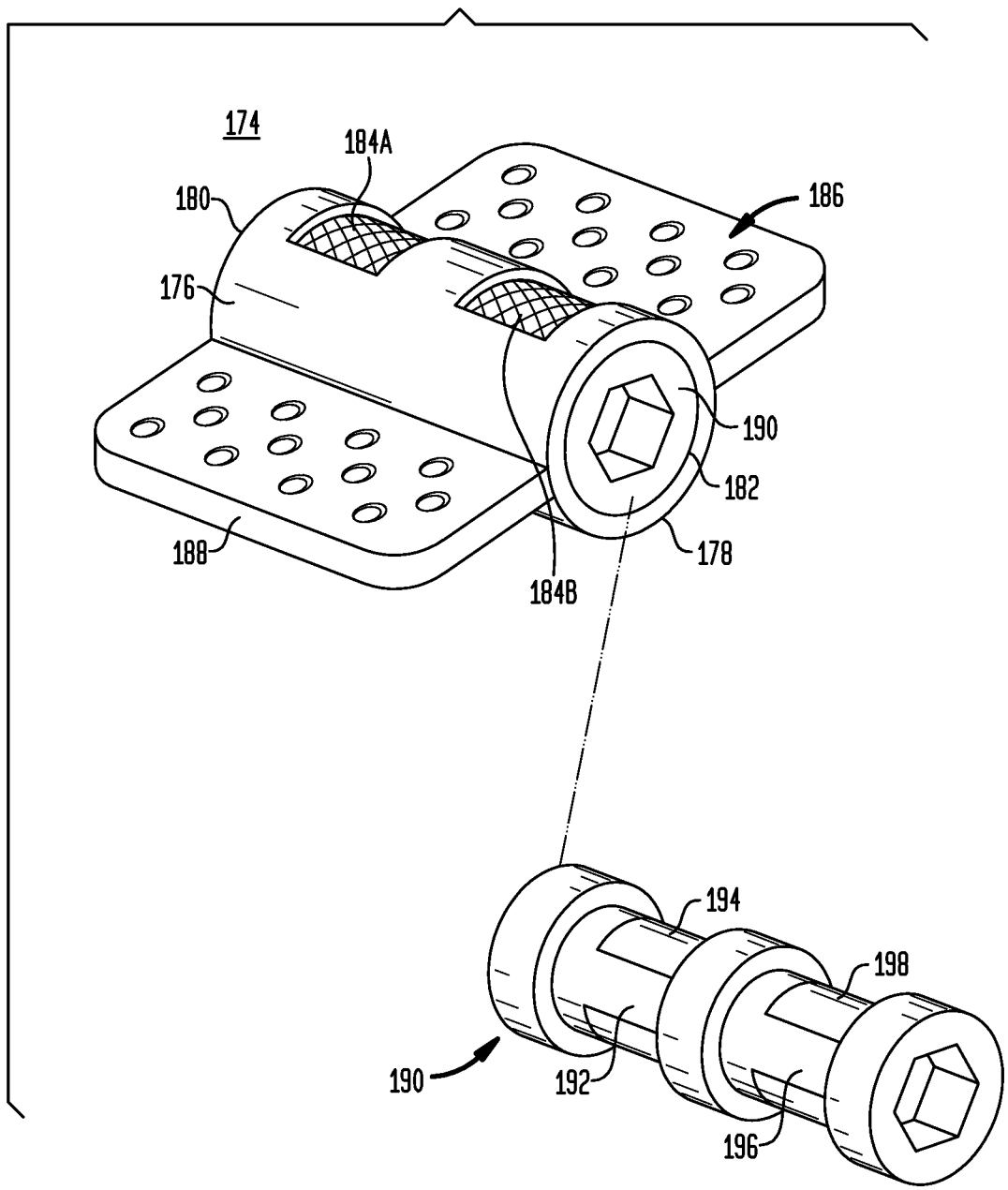
FIG. 7 shows a perspective view of a buttress with tensioning element of an implant for treating obstructive sleep apnea, in accordance with one embodiment of the present invention.

Referring to FIG. 7, in one embodiment, a system for treating obstructive sleep apnea includes an elongated element similar to that shown and described above in FIGS. 4A-4C and a second buttress 174 adapted to be implanted in inframandibular musculature.

In one embodiment, the elongated element of the implant FIG. 4A) is implanted in a patient's oral cavity with the first buttress implanted in a posterior region of a patient's tongue and the second buttress 174 implanted in or between the geniohyoid and/or mylohyoid muscles. The second buttress 174 may also be implanted between the digastrics and the mylohyoid muscles. Although the present invention is not limited by any particular theory of operation, it is believed that providing one or more additional buttresses implantable in the inframandibular musculature will improve the stability and effectiveness of the implant device.

Referring to FIG. 7, in one embodiment, the second buttress 174 includes a cylinder 176 having a first end 178, a second end 180, and a central opening 182 extending between the first and second ends 178, 180. The cylinder 176 includes a first radial opening 184A and a second radial opening 184B. The second buttress 174 also preferably includes a first flange 186 projecting from one side of the cylinder 176 and a second flange 188 projecting from an opposite side of the cylinder 176. The first and second flanges 186, 188 are preferably porous or covered with a porous film or fabric.

The second buttress 174 also preferably includes a tensioning element 190 that is received within the central opening 182 of the cylinder 176. In one embodiment, the tensioning element 190 is preferably a spool that may be rotated within the central opening 182 of the cylinder 176. The tensioning element 190 preferably includes a first section 192 having a first pierceable material 194 extending therethrough, and a second section 196 having a second pierceable material 198 extending therethrough. The first and second pierceable materials may include silicone, fabric, textile, and/or a solid polymer insert. In one embodiment, the first and second pierceable materials 194, 198 may be replaced by one or more wedge slots.

When the tensioning element 190 is inserted within the opening 182 of the cylinder 176, the first and second pierceable materials 194, 198 are preferably aligned with the first and second openings 184A, 184B of the cylinder 176. As will be described in more detail below, the free ends of the first and second arms of the elongated element are preferably passed through the respective first and second openings 184A, 184B and the first and second pierceable materials 194, 198 to couple the first and second arms of the implant with the tensioning element 190. The tensioning element 190 may then be rotated within the elongated opening 182 of the cylinder 176 to apply tension to the first and second arms of the implant.

Figure 8:
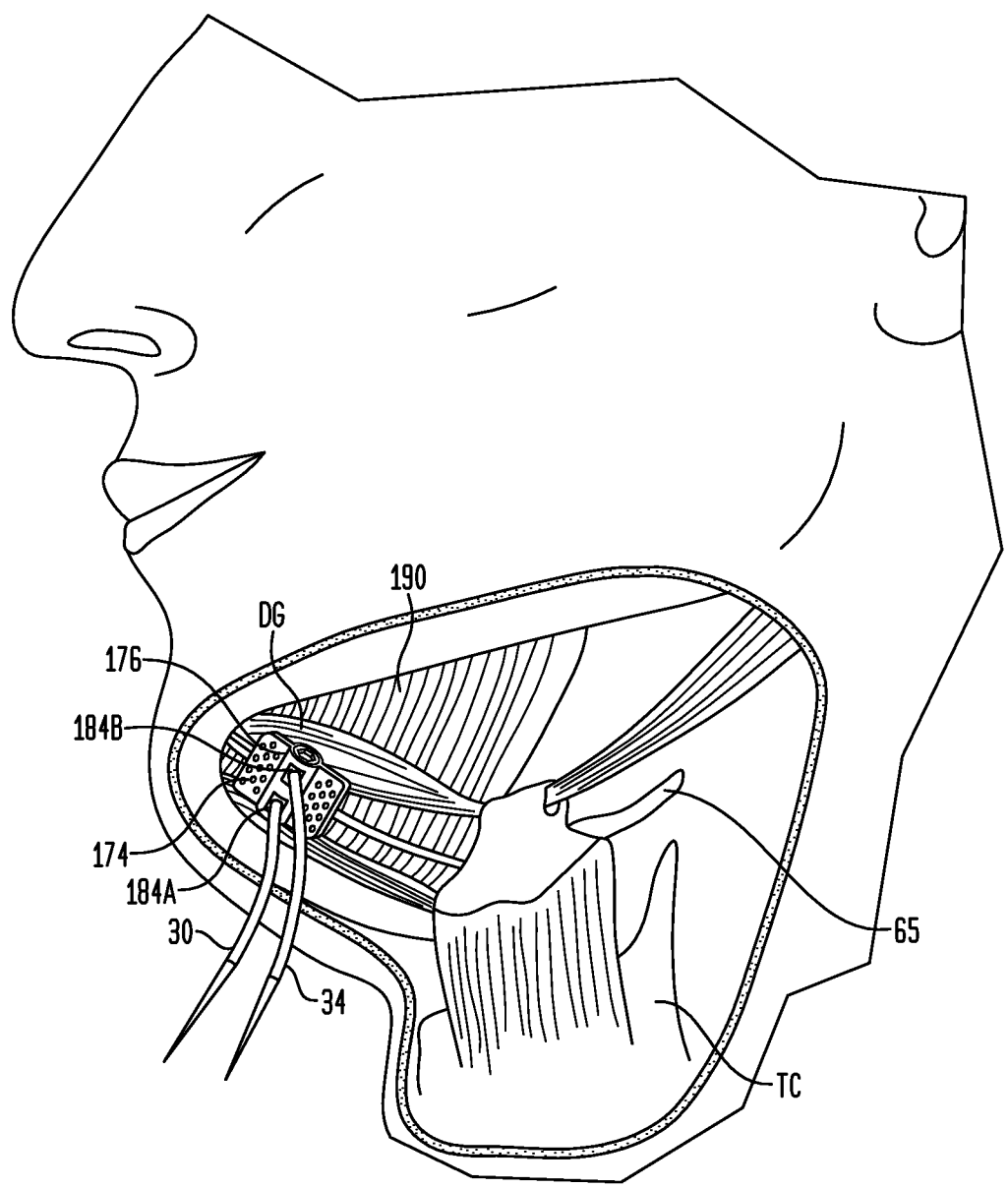
FIG. 8 shows a bottom perspective view of an implant for treating obstructive sleep apnea including the buttress with tensioning element of FIG. 7, in accordance with one embodiment of the present invention.

Referring to FIG. 8, in one embodiment, the second buttress 174 shown and described above in FIG. 7 is implanted within the inframandibular musculature of a patient. In one embodiment, the second buttress 174 is implanted between the digastric musculature DG and the geniohyoid musculature (not shown). As shown in FIG. 8, the digastric musculature DG is coupled with the hyoid bone 65 of the patient. The first and second arms 30, 34 of the implant shown in FIGS. 4A-4C are passed through the first and second openings 184A, 184B of the cylinder 176. The tensioning element 190 may be rotated to apply tension to the first and second arms 30, 34. As tension is applied to the first and second arms 30, 34, the first buttress implanted in the tongue (not shown) is pulled toward the second buttress 174 so that the base of the patient's tongue and the hyoid bone 65 are urged anteriorly for minimizing the likelihood of OSA episodes.

Figure 9:
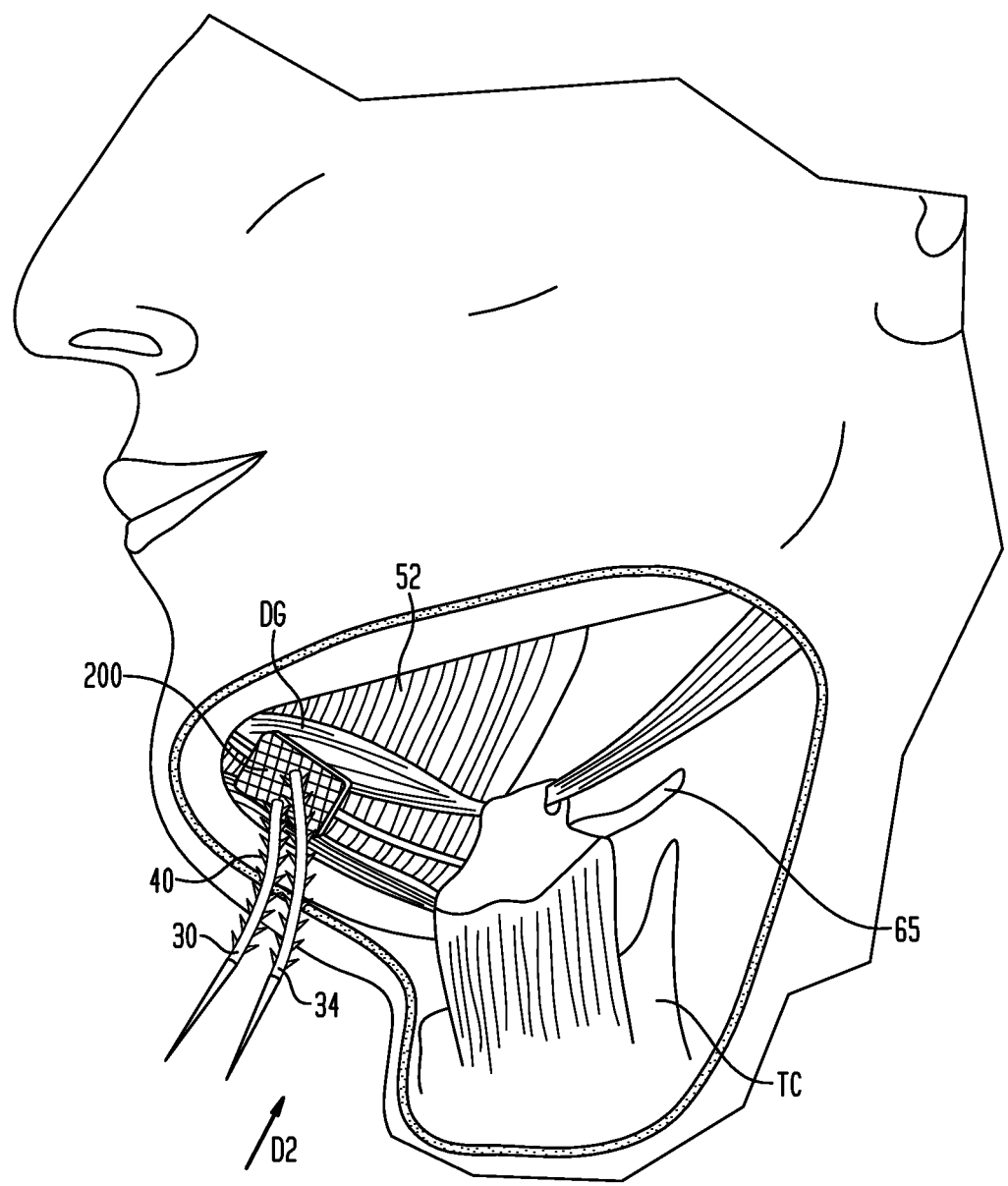
FIG. 9 shows a bottom perspective view of an implant for treating obstructive sleep apnea, in accordance with one embodiment of the present invention.

Referring to FIG. 9, in one embodiment, an implant for treating OSA includes a biocompatible pad 200 that is implanted in the inframandibular musculature. The biocompatible pad 200 preferably has a width and a length that provides a support base implantable in the inframandibular musculature. As shown in FIG. 9, the free ends of the first and second arms 30, 34 of the elongated element shown in FIG. 4A are passed through the mylohyoid musculature 52, the digastrics DG, and the biocompatible pad 200. As tension is applied to the free ends of the first and second arms 30, 34, the barbs 40 collapse inwardly and pass through the tissue and the biocompatible pad 200. After tension is applied to the arms 30, 34, the barbs 40 prevent the first and second arms 30, 34 from moving back in the direction designated $D_2$. Although the present invention is not limited by any particular theory of operation, it is believed that the presence of the barbs 40 enables tension to be applied through the first and second arms 30, 34 for urging the base of the tongue to move away from an opposing pharyngeal wall.

Figure 10:
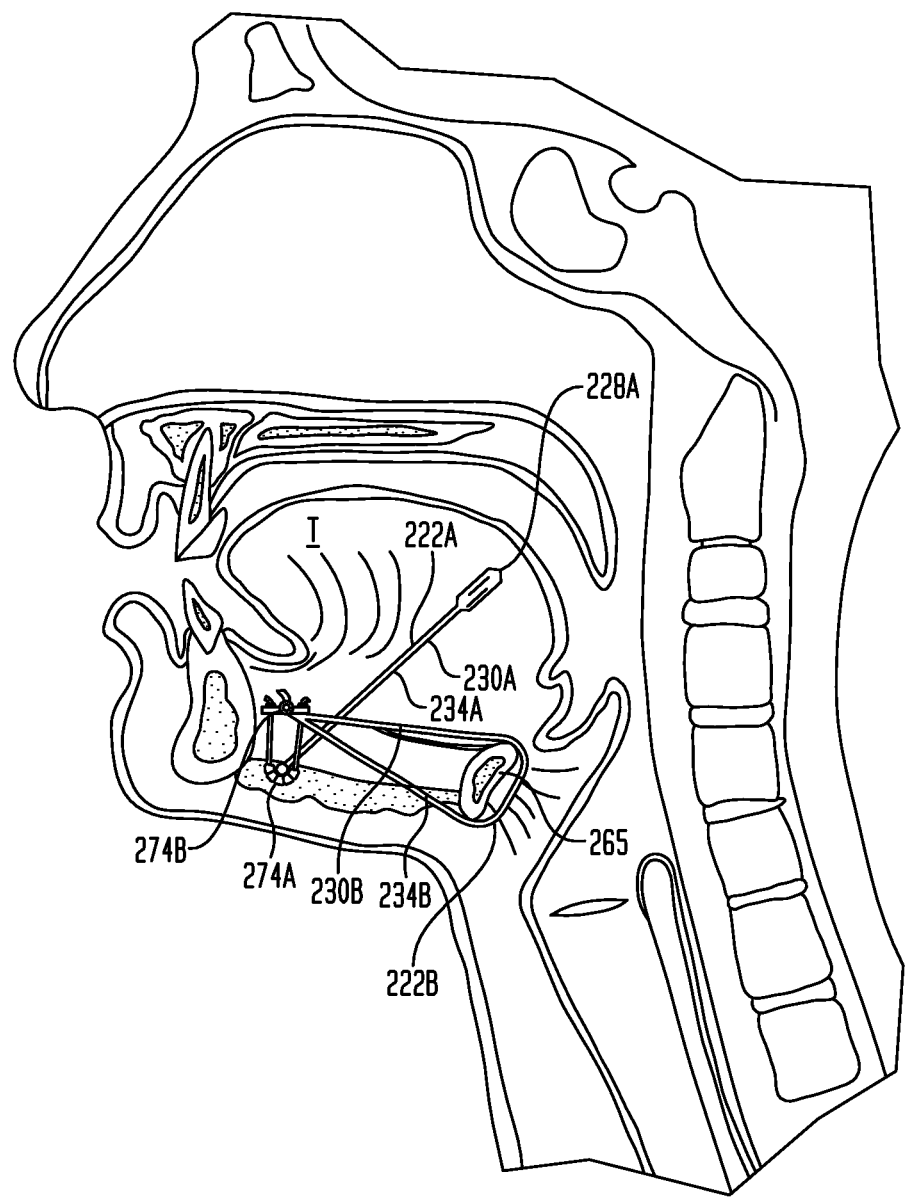
FIG. 10 shows a cross-sectional side view of implant system for treating obstructive sleep apnea, in accordance with one embodiment of the present invention.

Referring to FIG. 10, in one embodiment, a system for treating obstructive sleep apnea includes a first elongated element 222A having a buttress 228A implanted in the tissue of a tongue T. The first elongated element 228A includes first and second arms 230A, 234A projecting from the buttress 228A toward a second buttress 274A. The second buttress 274A has a structure that is substantially similar to the structure shown and described above in FIG. 7. The free ends of the first and second arms 230A, 234A of the first elongated element 222A are coupled with the tensioning element of the second buttress 274. The tensioning element of the second buttress 274 is rotatable for applying tension to the first elongated element 222A so as to move the base of the tongue T away from an opposing pharyngeal wall.

The system shown in FIG. 10 also preferably includes a third buttress 274B having a structure similar to the second buttress 274A. The system preferably includes a second elongated element 222B that is looped around a hyoid bone 265. The second elongated element 226B desirably includes a first arm 230B and a second arm 234B having respective free ends that are coupled with the third buttress 274B. The tensioning element of the third buttress 274B may be rotated for applying tension to the respective first and second arms 230B, 234B of the second elongated element 222B. Although the present invention is not limited by any particular theory of operation, it is believed that applying tension to the first and second arms 230B, 234B through the tensioning element of the third buttress 274B will move the hyoid bone 265 in an anterior direction so as to minimize the likelihood of an OSA episode.

Figure 11:
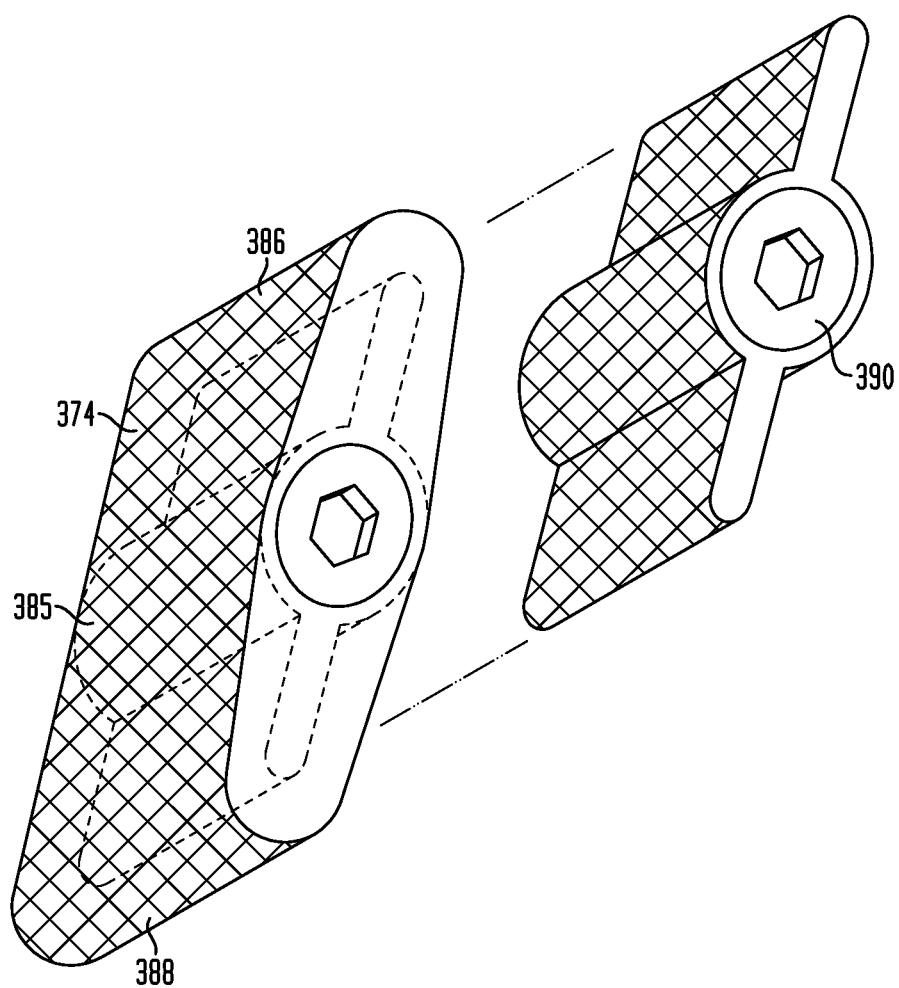
FIG. 11 shows a perspective view of a buttress with a tensioning element of an implant, in accordance with one embodiment of the present invention.

Referring to FIG. 11, in one embodiment, an implantable system for treating OSA may include a second buttress 374 having an elongated body having a posterior end 386 and an anterior end 388. The second buttress 374 may be used with the elongated implants described herein and in place of the second buttress structure shown and described above in FIG. 7. The second buttress 374 is preferably adapted to receive a tensioning element 390 for providing tension to first and second arms extending between a first buttress, e.g. the FIG. 4A embodiment, and the second buttress 374. As the tensioning element 390 is rotated, the free ends of the first and second arms of the elongated element are drawn toward the second buttress 374 for applying tension to the first and second arms, which, in turn, pulls the first buttress of the elongated element toward the second buttress 374. In one embodiment, the second buttress 374 comprises a mesh 385 that allows tissue in-growth for enhancing anchoring of the implant to body tissue.

Figure 12A:
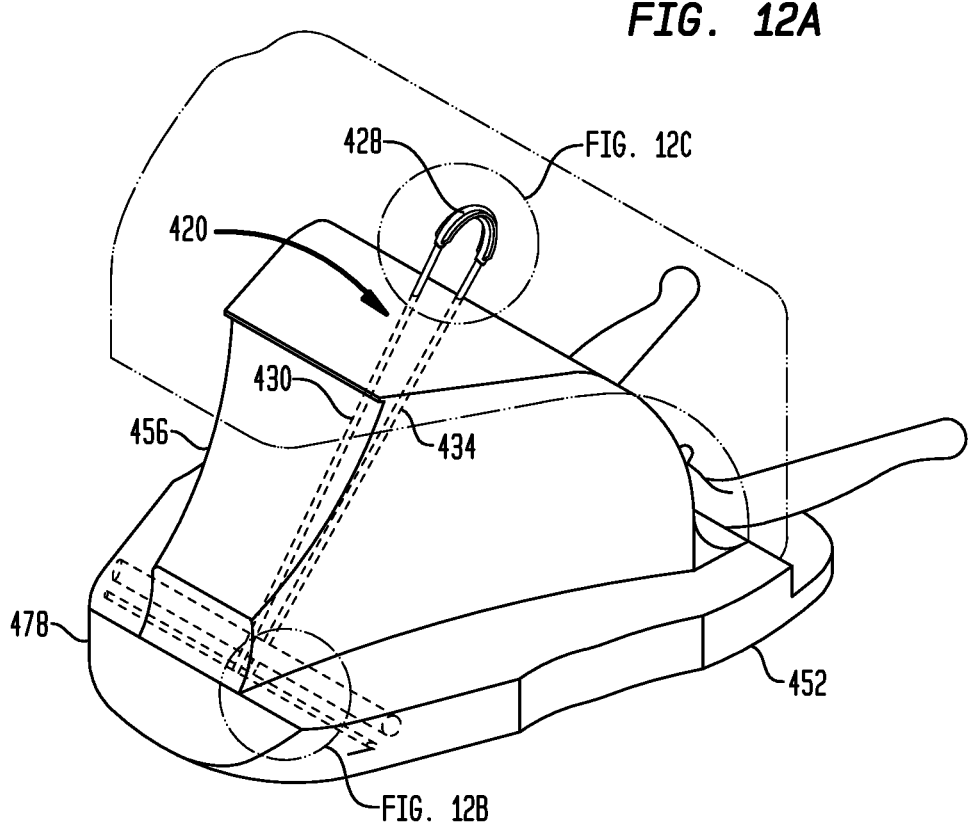
FIGS. 12A-12C show an implant for treating obstructive sleep apnea, in accordance with one embodiment of the present invention.
Figure 12B:
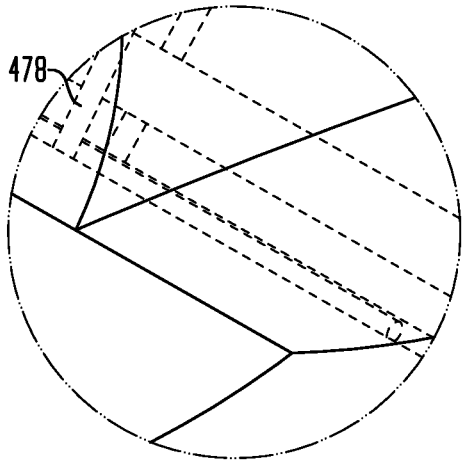
Figure 12C:
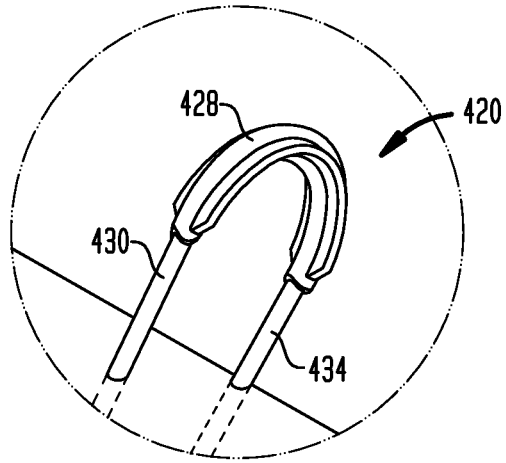

Referring to FIGS. 12A-12C, in one embodiment, an implant for treating obstructive sleep apnea includes a buttressed suture 420 having a central buttress 428 and first and second support arms 430, 434 extending from the central buttress 428. The first and second support arms 430, 434 may include barbs and/or braided, barbed regions. The distal ends of the first and second support arms 430, 434 are adapted to engage a second buttress 478 anchored in the tissue, muscles and/or cartilage of the patient. In one embodiment, the second buttress 478 is anchored in the inframandibular musculature of a patient. The distal ends of the support arms 430, 434 are preferably anchored to the second buttress 478 for applying tension to the first and second support arms 430, 434. Sufficient tension may be applied on the support arms for pulling the central buttress 428 toward the second buttress 478. FIG. 12C shows the buttressed suture 420 including the center buttress section 428 and the first and second support arms 430, 434 projecting from the central buttress 428. The center buttress section 428 preferably has a larger cross-sectioned area or a greater width than the first and second support arms 430, 434 for anchoring the implant in the tongue tissue and avoiding the "cheese-cutter" effect. In one embodiment, the buttress suture element is desirably installed in the midline of the tongue and is in the plane defined with a vertical loop orientation to capture the midline elements of tongue musculature only. The orientation of the buttress is superior to inferior within the midline which minimizes the possibility of nerve or vascular damage during installation.

Referring to FIG. 13, in one embodiment, a system for treating OSA includes a plurality of implant devices 520A, 520B, 520C. The implant devices 520A-520C may be similar to the implant device shown in FIGS. 12A-12C or any of the other implant devices disclosed herein. Each implant device 520A-520C preferably includes a respective central buttress 528A-528C and a pair of support arms 530A-530C projecting from opposite ends of the central buttresses. The implant devices 520A-520C may be parallel or angled relative to one another. The central buttresses are preferably positioned in the tongue 550 and the arms 530A-530C are preferably anchored in inframandibular musculature.

Referring to FIG. 14, in one embodiment, a system for treating OSA includes at least two implant devices 620A, 620B that cross one another. Each implant device preferably includes a central buttress 628A, 628B and a pair of support arms 630A, 630B projecting from opposite ends of the central buttresses. The implant devices are crossed so as to cross the planes of the fibers extending through the tongue 650 for maximizing engagement with the fibers.

Figure 15A:
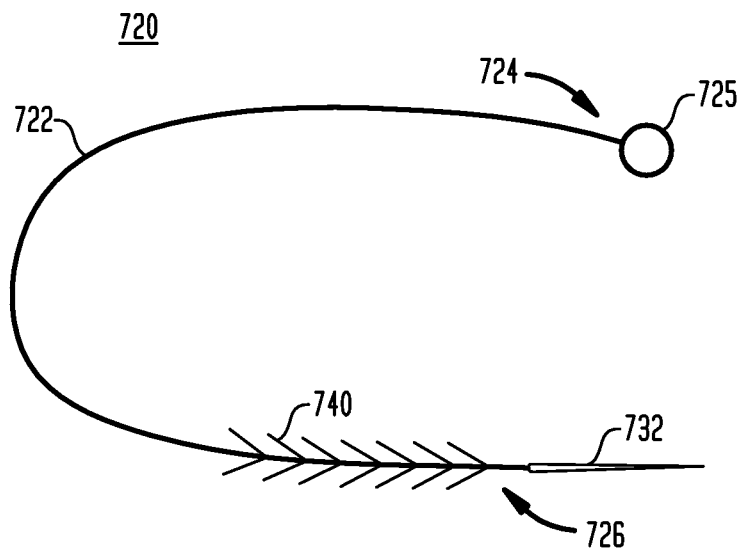
FIGS. 15A-15B show an implant for treating obstructive sleep apnea, in accordance with one embodiment of the present invention.

Referring to FIG. 15A, in one embodiment, a system for treating OSA includes a barbed suture 720 including an elongated element 722 having a first end 724 and a second end 726. The first end 724 of the elongated element 722 includes an enclosed loop 725 that is adapted to receive the opposing second end 726 of the elongated element 722. Although not shown, in other embodiments, an elongated element may include two or more closed loops provided along the length thereof. The implant 720 preferably includes a tissue piercing element 732 secured to the second end 726 of the elongated element 722 for advancing the elongated element through tissue. The elongated element 722 desirably includes at least one set of barbs 740 projecting therefrom.

Figure 15B:
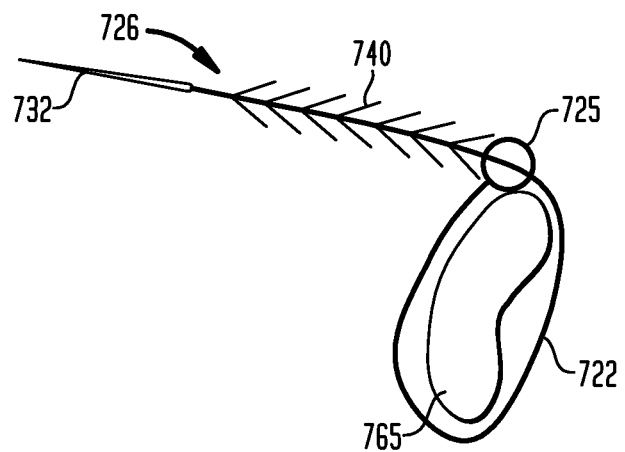

Referring to FIG. 15B, in one embodiment, the elongated element 722 may be used for treating OSA by passing the elongated element 722 around a hyoid bone 765 and passing the tissue piercing element 732 and one or more of the barbs 740 through the enclosed loop 725 at the first end of the elongated element 722. Tension may be applied to the second end 726 of the elongated element 722 for urging the hyoid bone 765 to move anteriorly and/or inferiorly. Although FIG. 15B shows the elongated element looped around the hyoid bone, the elongated element may be looped around other structures located in or adjacent the oral cavity for urging the base of the tongue and/or the hyoid bone away from the posterior region of the pharyngeal wall.

In one embodiment of the present invention, a system for treating OSA includes an elongated element that is wrapped around fibers such as muscle fibers extending through a tongue. In one embodiment, the fibers are preferably muscle fibers that extend in a generally vertical direction though the tongue, such as genioglossus muscle fibers. As used in this embodiment, the term "vertical" describes a direction relative to upper and lower ends of a human body. The elongated element is preferably looped around the muscle fibers at least once so as to capture the muscle fibers within the loop. The looped elongated element may extend in a substantially horizontal plane relative to the vertically extending fibers. After a bundle of muscle fibers have been captured within the looped elongated element, the muscle fibers are desirably compacted or compressed together by the elongated element. In one embodiment, tension may be applied to a free end of the elongated element for moving the tongue away from an opposing pharyngeal wall. The free end of the elongated element may be anchored in inframandibular musculature for maintaining the tongue in a forward shifted position so that the back of the tongue does not collapse against the opposing pharyngeal wall during sleep.

Referring to FIG. 16, in one embodiment, an implant system for treating OSA includes an elongated element 822 implanted within an oral cavity of a patient The oral cavity typically includes a body of a tongue T, a mylohyoid muscle 852, a geniohyoid muscle 854, and a genioglossus muscle 856. The mylohyoid muscle 852 has an anterior end 858 anchored to a mandible 860 and a posterior end anchored to a hyoid bone (not shown). The elongated element 822 preferably has a first end 824 with an opening 825, a buttress 828 adjacent the opening 825, a second end 826, and barbs 840. The barbs 840 preferably project from the elongated element 822 between the second end 826 of the elongated element and the buttress 828. In one embodiment, the second end 826 of the elongated element is passed through the opening 825 to form a loop around fibers extending through the tongue T, and the second end 826 of the elongated element 822 is pulled toward the inframandibular musculature. In one embodiment, tension is applied to the second end 826 of the elongated element 822 so as to further compress the fibers located within the loop 845 and for shifting the base of the tongue in an anterior and/or inferior direction. The second end 826 of the elongated element 822 is desirably anchored in the inframandibular musculature for maintaining the position of the tongue away from an opposing pharyngeal wall. In one embodiment, the elongated element may not have a buttress.

Referring to FIG. 17, in one embodiment, an implant system for treating OSA includes an elongated element 922 having a first end 924, a second end 926, and a buttress 928 disposed between the first and second ends. In one embodiment, the buttress 928 desirably forms the widest portion of the implant. The elongated element 922 preferably includes a first arm 930 located between the buttress 928 and the first end 924, and a second arm 934 extending between the buttress 928 and the second end 926 thereof. Tissue piercing elements (not shown) may be secured to the free ends of the respective first and second arms 930, 934. In one embodiment, the elongated element may have one or more features found in the implant shown and described above in FIGS. 4A-4C.

Referring to FIG. 17, in one embodiment, the buttress area 928 of the elongated element is wrapped around fibers, such as muscle fibers, extending through the tongue T to form a loop 945 that surrounds the fibers. The fibers may be genioglossus muscle fibers. After the loop 945 is formed, the free ends 924, 926 of respective first and second arms 930, 934 are advanced through the tongue tissue toward the inframandibular musculature. Tension is applied to the free ends 924, 926 of the first and second arms so as to compress the bundle of fibers within the loop 945. In one embodiment, tension is applied to the free ends of the first and second arms 930, 934 so as to displace the tongue in an anterior and/or inferior direction for minimizing the likelihood of OSA events. The ends of the first and second arms are preferably anchored in inframandibular musculature using one or more features from any of the embodiments disclosed herein.

In one embodiment, a biocompatible element is looped around fibers such as genioglossus fibers extending through a tongue. The biocompatible element may include a ring-like device having an opening at one side for enabling fibers to be positioned within the ring-like structure. After fibers are positioned within the ring-like structure, the open end of the ring-like structure may be closed and the ring tightened around the surrounded fibers for compressing the fibers within the ring-like structure. A tether or elongated element may be coupled with the ring-like structure. A distal end of the tether may be advanced toward the inframandibular musculature and tension may be applied to the tether for pulling the ring-like structure in an anterior and/or inferior direction. The tether may be anchored in inframandibular musculature for shifting the tongue away from an opposing pharyngeal wall.

Although the above-described embodiments are not limited by any particular theory of operation, it is recognized that muscle fibers in the tongue extend in a generally vertical direction as they terminate near the superior mucosal surface of the tongue. As such, a horizontally-extending band or loop may be secured around a bundle of these vertically-extending fibers and the band or loop may be pulled in an anterior and/or inferior direction for shifting the position of the tongue. A tether or elongated element may also be coupled with the band or loop, with a lower end of the tether or elongated element anchored in inframandibular musculature to maintain the tongue in a forward shifted position so that the back of the tongue remains spaced from an opposing pharyngeal wall.

For clarity, many of the embodiments shown in the drawing figures depict elongated elements that are monofilaments. In one or more embodiments, however, the elongated elements may include a braided element with or without barbs, a woven structure with or without barbs, and/or a circular knit structure with or without barbs. In certain preferred embodiments, the elongated element may incorporate one or more of the features disclosed in commonly assigned U.S. Patent Application Publication Nos. 20070005109 and 20070005110, the disclosures of which are hereby incorporated by reference herein.

In one embodiment, a patient is prepared for surgery using local or general anesthesia. The first arm 30 of the barbed suture (FIG. 4A) is advanced in a lateral direction through the posterior portion of the tongue until the center buttressed portion 28 of the barbed suture is centered in the tongue 50. The needle at the end of the first support arm 30 is preferably passed within the tongue from the posterior portion of the tongue through a generally anterior and inferior direction to engage the inframandibular musculature. The needle facilitates advancement of the first support arm through the tissue of the tongue T. The second support arm 34 is advanced through the tissue of the tongue in a similar manner with the needle that is attached at the free end of the second support arm 34.

In one embodiment, the distal or free ends of the support arms are adapted to be attached to soft tissue located between the hyoid bone and the mandible. In one embodiment, a small diameter trocar may be advanced through the floor of the mouth near the base of the tongue. A snare is preferably introduced through the lumen of the trocar to grab each of the support arms. The support arms are preferably pulled through the trocar and the trocar is removed. A surgeon may pull the distal ends of the support arms until the posterior surface of the tongue is advanced in an anterior direction so that it is unlikely to form a seal against the back wall of the pharynx. The distal ends of the support arms may be attached to the soft tissues of the inframandibular region to set the tongue in the new position. The distal ends of the support arms may be attached to soft tissue or musculature such as the geniohyoid muscle through the use of barbs on the device, glue, sutures, or any combination thereof, or the knotting together of the two free ends of the support arms to capture the encircled musculature.

In one embodiment, the free ends of the barbed suture are intended to be attached to the hyoid bone and/or the thyroid cartilage. In this embodiment, a small diameter trocar is advanced through an incision that is previously placed near a horizontal crease of skin just below the hyoid bone and up to the base of the tongue. A snare is preferably introduced through a lumen in the trocar to grab each free end of the barbed suture. The free ends of the device are preferably pulled through the trocar and the trocar is removed. A surgeon may pull the free ends of the barbed suture until the posterior surface of the tongue is advanced slightly to ensure that it is unlikely to or cannot form a seal against the posterior wall of the pharynx.

In one embodiment, an implant having two, three, or more buttressed sections placed at various tissue sites may be used. In this embodiment, a surgeon may form small incisions within creases of skin and place the buttress components in desired locations in a minimally invasive manner. The entire system may be locked in place using self-locking devices or a mechanism that allows the surgeon to adjust each buttress independently, or with the use of self-locking nuts. In one embodiment, mesh-like tubes may be used instead of solid polymeric devices. A multi-buttress concept may also be used independently with no center attachment device. The ends of the multiple buttresses may be knotted together to secure all three ends independent from the opposing side of the buttresses.

The present invention provides a number of advantages over prior art methods and devices used for treating obstructive sleep apnea syndrome and hypopnea. First, the methods, systems and devices disclosed herein provide for simple surgical procedures that are minimally invasive. Typically, the methods, systems and devices disclosed herein may be utilized during an outpatient procedure. In addition, the methods, systems and devices disclosed herein provide both immediate and long term results for treating obstructive sleep apnea syndrome and hypopnea. Moreover, the methods, systems and devices disclosed herein do not require a significant level of patient compliance.

In addition, the present invention does not anchor the posterior aspect of the tongue to a fixed hard structure, such as the mandible and is only preferably fixated within and or against soft tissues. Thus, the present invention is significantly less likely to affect swallowing or speech, thereby providing a great improvement over prior art devices, systems and methods. The present invention also preferably uses materials having long-term biocompatibility.

Although various embodiments disclosed herein relate to use in humans, it is contemplated that the present invention may be used in all mammals, and in all animals having air passages. Moreover, the methods, systems and devices disclosed herein may incorporate any materials that are biocompatible, as well as any solutions or components that minimize rejection, enhance tissue ingrowth, enhance the formation of mucosal layers, and improve acceptance of the device by a body after the device has been implanted.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A method of treating obstructive sleep apnea comprising:
    providing an elongated element including a central area having first and second ends, a first arm extending from the first end of the central area, and a second arm extending from the second end of the central area, said first and second arms having integral anchoring elements provided at distal, free ends of said first and second arms;
    implanting the central area of said elongated element in a tongue;
    advancing said first and second arms through said tongue until said distal, free ends of said first and second arms engage inframandibular musculature;
    applying tension to said first and second arms for moving a posterior surface of said tongue away from an opposing surface of a pharyngeal wall;
    directly engaging soft tissue in the inframandibular musculature with said integral anchoring elements provided at said distal, free ends of said first and second arms for anchoring said first and second arms to the inframandibular musculature.

2. The method as claimed in claim 1, further comprising:
    wrapping said elongated element around muscle fibers extending through said tongue so as to form at least one loop about the muscle fibers;
    using the at least one loop for compacting the muscle fibers wrapped by said elongated element.

3. The method as claimed in claim 1, wherein said integral anchoring elements provided at said distal, free ends of said first and second arms are selected from the group consisting of sutures, clips, staples, barbs, and adhesive.

4. The method as claimed in claim 1, wherein said central area of said elongated element comprises a buttress defining a larger width region of said elongated element.

5. The method as claimed in claim 4, wherein after the implanting step said buttress extends along an axis that traverses an anterior-posterior axis of said tongue.

6. The method as claimed in claim 4, further comprising implanting a second buttress in the inframandibular musculature and coupling said first and second arms with said second buttress.

7. The method as claimed in claim 1, wherein said integral anchoring elements comprise a first set of barbs projecting from said first arm and a second set of barbs projecting from said second arm.

8. The method as claimed in claim 7, wherein said elongated element is a braided structure and said first and second sets of barbs extend through interstices of said braided structure.

9. The method as claimed in claim 1, wherein said integral anchoring elements comprise barbs and wherein during the anchoring step said barbs directly engage the soft tissue in the inframandibular musculature.

10. The method as claimed in claim 1, wherein said integral anchoring elements comprise soft anchor barbs, and wherein the method further comprises pulling said first and second arms in a first direction through the soft tissue in the inframandibular musculature for collapsing said soft anchor barbs inwardly.

11. A method of treating obstructive sleep apnea comprising:
providing an elongated element including a central buttress area having a first end and a second end, a first arm extending from the first end of said central buttress area, and a second arm extending from the second end of said central buttress area, said first and second arms having integral anchoring elements provided at distal, free ends thereof, wherein said central buttress area has a larger cross-sectional width than said first and second arms;
implanting said central buttress area of said elongated element in a tongue so that a longitudinal axis of said central buttress area intersects an anterior-posterior axis of said tongue;
advancing said first and second arms through said tongue until said distal, free ends of said first and second arms engage the inframandibular musculature;
applying tension to said first and second arms for pulling said central buttress area toward the inframandibular musculature so as to move a posterior surface of said tongue away from an opposing surface of a pharyngeal wall;
anchoring said first and second arms to the inframandibular musculature, wherein said tissue anchoring elements provided at said distal, free ends of said first and second arms directly engage soft tissue in the inframandibular musculature for providing a soft tissue anchor for said implant.

12. The method as claimed in claim 11, further comprising:
wrapping the central buttress area of said elongated element around muscle fibers extending through said tongue so as to form at least one loop about the muscle fibers;
using the at least one loop for compacting the muscle fibers wrapped by said central buttress area.

13. The method as claimed in claim 11, further comprising looping at least one of said first and second arms around a hyoid bone.

14. The method as claimed in claim 11, further comprising passing at least one of said first and second arms through cartilage located below a hyoid bone.

15. The method as claimed in claim 11, wherein said tissue anchoring elements on said first arm comprise a first set of barbs projecting therefrom and said tissue anchoring elements on said second arm comprise a second set of barbs projecting.

16. The method as claimed in claim 11, wherein said elongated element comprises a braided element with a first set of barbs projecting from said first arm and a second set of barbs projecting from said second arm.

17. The method as claimed in claim 11, wherein said integral anchoring elements comprise soft anchor barbs, and wherein the method further comprises pulling said first and second arms in a first direction through the soft tissue in the inframandibular musculature for collapsing said soft anchor barbs inwardly.

18. The method as claimed in claim 11, further comprising implanting a biocompatible pad in inframandibular musculature, wherein said tissue anchoring elements directly engage said biocompatible pad for providing a soft tissue anchor for said implant.

* * * * *